US012344646B2

United States Patent
Cai et al.

(10) Patent No.: US 12,344,646 B2
(45) Date of Patent: Jul. 1, 2025

(54) ANTIBODY-TNF α FUSION PROTEIN AND ITS PREPARATION AND APPLICATIONS

(71) Applicant: Bang Ding, Shanghai (CN)

(72) Inventors: Zeling Cai, Shanghai (CN); Yi Chen, Shanghai (CN)

(73) Assignee: Bang Ding, Shanghai (CN)

( * ) Notice: Subject to any disclaimer, the term of this patent is extended or adjusted under 35 U.S.C. 154(b) by 1026 days.

(21) Appl. No.: 17/413,260

(22) PCT Filed: Dec. 13, 2018

(86) PCT No.: PCT/CN2018/120839
§ 371 (c)(1),
(2) Date: Jun. 11, 2021

(87) PCT Pub. No.: WO2020/118605
PCT Pub. Date: Jun. 18, 2020

(65) Prior Publication Data
US 2022/0098262 A1    Mar. 31, 2022

(51) Int. Cl.
| | | |
|---|---|---|
| C07K 14/525 | (2006.01) | |
| A61K 31/45 | (2006.01) | |
| A61K 31/704 | (2006.01) | |
| A61K 38/12 | (2006.01) | |
| A61K 38/19 | (2006.01) | |
| A61K 39/00 | (2006.01) | |
| A61K 39/395 | (2006.01) | |
| A61K 45/06 | (2006.01) | |
| A61P 35/00 | (2006.01) | |
| C07K 16/28 | (2006.01) | |
| C07K 16/32 | (2006.01) | |

(52) U.S. Cl.
CPC ............ *C07K 14/525* (2013.01); *A61K 31/45* (2013.01); *A61K 31/704* (2013.01); *A61K 38/12* (2013.01); *A61K 38/191* (2013.01); *A61K 39/3955* (2013.01); *A61K 39/39558* (2013.01); *A61K 45/06* (2013.01); *A61P 35/00* (2018.01); *C07K 16/2863* (2013.01); *C07K 16/32* (2013.01); *A61K 2039/505* (2013.01); *C07K 2317/14* (2013.01); *C07K 2317/24* (2013.01); *C07K 2317/73* (2013.01); *C07K 2319/02* (2013.01); *C07K 2319/30* (2013.01)

(58) Field of Classification Search
None
See application file for complete search history.

(56) References Cited

U.S. PATENT DOCUMENTS

2003/0187225 A1* 10/2003 Penichet ............ C07K 14/5434
530/391.1

FOREIGN PATENT DOCUMENTS

| CN | 1374871 | 10/2002 |
|---|---|---|
| CN | 103833856 | 6/2014 |
| JP | H07223968 A | 8/1995 |
| WO | 0107081 | 2/2001 |
| WO | 03068924 | 8/2003 |
| WO | 2006115800 | 11/2006 |

OTHER PUBLICATIONS

Almagro & Fransson, Humanization of antibodies, Frontiers in Bioscience 2008; 13: 1619-33 (Year: 2008).*
Bowie et al., Deciphering the Message in Protein Sequences: Tolerance to Amino Acid Substitutions, Science, 1990, 247:1306-1310 (Year: 1990).*
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biol. 111:2129-2138, 1990 (Year: 1990).*
Lazar et al., Transforming Growth Factor ox: Mutation of Aspartic Acid 47 and Leucine 48 Results in Different Biological Activities, Mol. Cell. Biol., 8:1247-1252, 1988 (Year: 1988).*
Rudikoff et al., Single amino acid substitution altering antigen-binding specificity, PNAS, USA, 1982, 79: 1979-1983 (Year: 1982).*
Colman, Effects of amino acid sequence changes on antibody-antigen interactions, Research in Immunology, vol. 145, Issue 1, pp. 33-36 (Year: 1994).*
Ibragimova and Wade, Stability of the—Sheet of the WW Domain: A Molecular Dynamics Simulation Study, Biophysical Journal, Oct. 1999, vol. 77, 2191-2198, Publication Date: Oct. 1999 (Year: 1999).*
Lin et al., Construction and Functional Study of a Novel Anti HER2/neu-hTNF-a Immunotoxin, Prog. Biochem. Biophys., 32 (9), 850-856, Publication Year: 2005 (Year: 2005).*
Ortiz-Sanchez et al., Antibody—cytokine fusion proteins: applications in cancer therapy, Expert Opin. Biol. Ther. 8(5): 609-632, Publication Date: Apr. 13, 2008 (Year: 2008).*
TNFgenecards downloaded from: https://www.genecards.org/cgi-bin/carddisp.pl?gene=TNF, on Aug. 23, 2024 (Year: 2024).*
First Office Action issued for Chinese Patent Application No. 201880092569.1, dated Mar. 29, 2023, 12 pages including English machine translation.
Second Office Action issued for Chinese Patent Application No. 201880092569.1, dated Oct. 28, 2023, 10 pages including partial English machine translation.
International Search Report issued for International Patent Application No. PCT/CN2018/120839, Date of mailing: Sep. 11, 2019, 12 pages including English translation.

(Continued)

*Primary Examiner* — Peter J Reddig
*Assistant Examiner* — Cheng Lu
(74) *Attorney, Agent, or Firm* — HSML P.C.

(57) ABSTRACT

Provided is an antibody-tumor necrosis factor α fusion protein and its preparation and applications. Specifically, the present disclosure relates to a fusion protein comprising an antibody moiety and a TNFα moiety, a nucleic acid molecule encoding same, a nucleic acid construct, a host cell and a method of production thereof, as well as applications of these materials in prevention and/or treatment of tumors.

4 Claims, 9 Drawing Sheets
Specification includes a Sequence Listing.

(56) References Cited

OTHER PUBLICATIONS

Bauer, S. et al., "Targeted Bioactivity of Membrane-Anchored TNF by an Antibody-Derived TNF Fusion Protein," The Journal of Immunology, vol. 172, 2004, pp. 3930-3939. Cited in PCT International Search Report.

Christ, O. et al., "Efficacy of Local versus Systemic Application of Antibody-Cytokine Fusion Proteins in Tumor Therapy," Clinical Cancer Research, vol. 7, Apr. 2001, pp. 985-998. Cited in PCT International Search Report.

Hoogenboom, H. R. et al., "Construction and Expression of Antibody-Tumor Necrosis Factor Fusion Proteins," Molecular Immunology, vol. 28, No. 9, 1991, pp. 1027-1037. Cited in PCT International Search Report.

Han, H. et al., "Construction and expression of the fusion protein consisting of human melanoma specific McAb VH and human Tnf," J Fourth Milit Med Univ, 19(1), 1998, pp. 15-17 (with English abstract).

Roberts, N. J. et al., "Systemic use of tumor necrosis factor alpha as an anticancer agent," Oncotarget, vol. 2, No. 10, 2011, pp. 739-751.

Balkwill, F., "Tumor Necrosis Factor, Improving on the formula," Nature, vol. 361, 1993, pp. 206-207.

Tracey, K. J. et al., "Tumor Necrosis Factor, Other Cytokines and Disease," Ann. Rev. Cell Biol., 1993, 9:317-343.

Hoogenboom, H. R. et al., "Construction and Expression of Antibody-Tumor Necrosis Factor Fusion Proteins," Molecular Immunology, vol. 28, No. 9, 1991, pp. 1027-1037.

Di Matteo, P. et al., "Anti-metastatic activity of the tumor vascular targeting agent NGR-TNF," Clin. Exp. Metastasis., 32 (3), 2015, pp. 289-300.

Loetscher, H. et al., "Human Tumor Necrosis Factor alpha (TNF alpha) Mutants with Exclusive Specificity for the 55-kDa or 75-kDa TNF Receptors," The Journal of Biological Chemistry, vol. 268, No. 35, 1993, pp. 26350-26357.

Baselga, J. et al., "Critical Update and Emerging Trends in Epidermal Growth Factor Receptor Targeting in Cancer," Journal of Clinical Oncology, vol. 23, No. 11, 2005, pp. 2445-2459.

Hudis, C. A., "Trastuzumab—Mechanism of Action and Use in Clinical Practice," The New England Journal of Medicine, 357;1, 2007, pp. 39-51.

\* cited by examiner

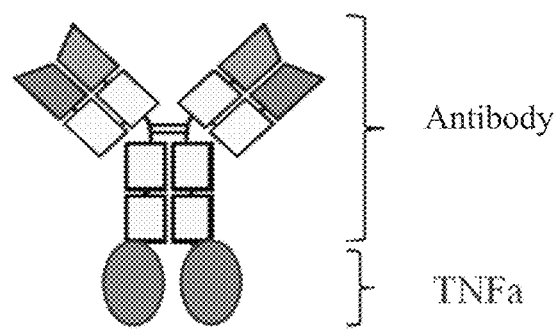
FIG. 1
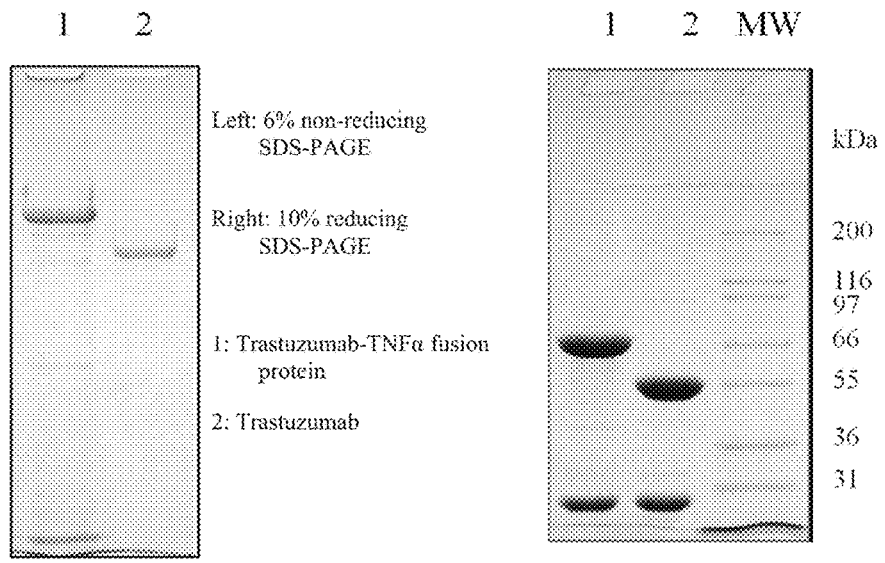
FIG. 2A
FIG. 2B
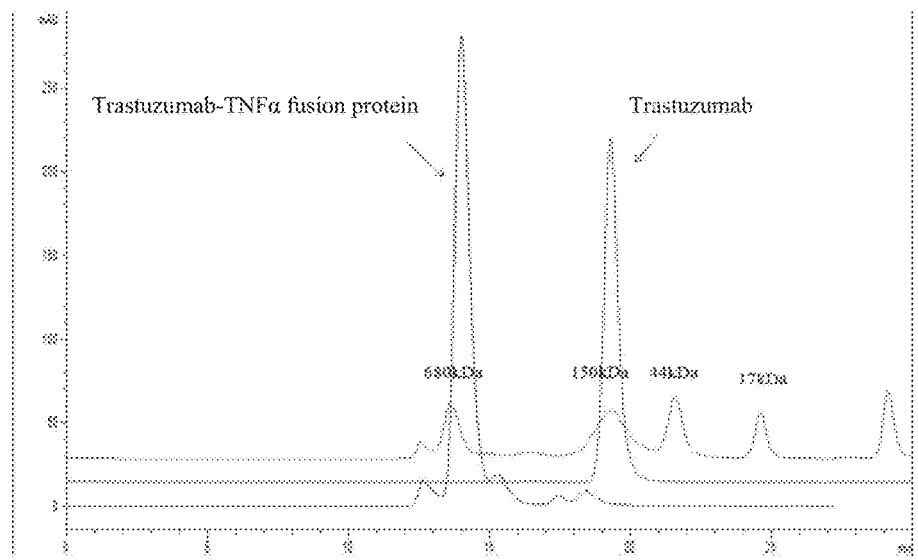
FIG. 2C

A: 6% non-reducing SDS-PAGE

B: 10% reducing SDS-PAGE

1: Cetuximab-TNFα fusion protein
2: IgG1

SEQUENCE LISTING

```
<160> NUMBER OF SEQ ID NOS: 22

<210> SEQ ID NO 1
<211> LENGTH: 1878
<212> TYPE: DNA
<213> ORGANISM: Artificial
<220> FEATURE:
<223> OTHER INFORMATION: Sequence encoding Trastuzumab's heavy chain-TNF
      alpha

<400> SEQUENCE: 1
atggagtttg gtctgtcctg gctgtttctg gtggctatcc tgaagggagt gcagtgcgaa        60
gtgcagctgg tcgaatctgg gggagggctg gtgcagccag gaggatcact gaggctgtcc       120
tgcgccgcta gcgggttcaa catcaaggac acctacattc actgggtcag acaggctcct       180
ggcaagggac tggagtgggt ggcacgcatc tatccaacta atgggtacac cagatatgcc       240
gactctgtga agggtcggtt taccatttct gcagatacaa gtaaaaacac tgcctacctg       300
cagatgaact ccctgcgagc cgaagataca gccgtgtact attgcagtcg ttgggggggt       360
gacggattct acgctatgga ttattggggg cagggcaccc tggtcacagt gtccagcgca       420
tcaacaaagg ggccttccgt gtttccactg gccccctcta gtaaaagcac ctctggcgga       480
acagcagccc tgggttgtct ggtgaaggac tacttcccag agccagtcac cgtgtcctgg       540
aacagcggcg ccctgacatc cggagtccat acttttcctg ctgtgctgca gtcatccggg       600
ctgtacagcc tgagctctgt ggtcactgtc ccaagttcat ccctgggtac tcagacctat       660
atctgcaacg tgaatcacaa gccatccaat accaaagtgg acaagaaagt ggagcccaag       720
agctgtgata aaacacatac ttgcccccct tgtcctgcac agaactgctg ggaggtcca        780 tccgtgttcc tgtttccacc caagcctaaa gacaccctga tgatttctcg aactccagag       840
gtcacctgcg tggtcgtgga cgtgtcccac gaggacccg aagtcaagtt caactggtac        900
gtggatggcg tcgaagtgca taatgctaag acaaaaccaa gagaggaaca gtacaacagc       960
acttatcgcg tcgtgtctgt cctgaccgtg ctgcaccagg attggctgaa cggcaaggag      1020
tataagtgca agtgagcaa taaggctctg cccgcaccta tcgagaaaac aatttctaag      1080
gctaaaggac agcctaggga accacaggtg tacactctgc ctccatctcg ggaggaaatg      1140 accagaacc aggtcagtct gacatgtctg gtgaaaggct tctatccctc cgacatcgca       1200
gtggagtggg aaagcaatgg acagcctgag aacaattaca gaccacacc ccctgtgctg       1260 gactctgatg gcagtttctt tctgtatagt aagctgaccg tggataaatc acggtggcag      1320
cagggaaatg tctttagttg ttcagtgatg cacgaagcac tgcacaatca ctacactcag      1380
aaatcactgt cactgtcccc aggagtcaga tcatcttctc gaacccgag tgacaagcct       1440 gtagcccatg ttgtagcaaa ccctcaagct gaggggcagc tccagtggct gaaccgccgg      1500
gccaatgccc tcctggccaa tggcgtggag ctgagagata ccagctggt ggtgccatca       1560
```

```
gagggcctgt acctcatcta ctcccaggtc ctcttcaagg gccaaggctg cccctccacc    1620
catgtgctcc tcacccacac catcagccgc atcgccgtct cctaccagac caaggtcaac    1680
ctcctctctg ccatcaagag cccctgccag agggagaccc cagaggggc tgaggccaag    1740 ccctggtatg agcccatcta tctgggaggg gtcttccagc tggagaaggg tgaccgactc    1800
agcgctgaga tcaatcggcc cgactatctc gactttgccg agtctgggca ggtctacttt    1860
gggatcattg ccctgtga                                                   1878
```

<210> SEQ ID NO 2
<211> LENGTH: 625
<212> TYPE: PRT
<213> ORGANISM: Artificial
<220> FEATURE:
<223> OTHER INFORMATION: Amino acid sequence of Trastuzumab's heavy
      chain-TNF alpha

<400> SEQUENCE: 2

```
Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300
```

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Val Arg Ser Ser Ser Arg Thr Pro Ser Asp Lys Pro
465                 470                 475                 480

Val Ala His Val Val Ala Asn Pro Gln Ala Glu Gly Gln Leu Gln Trp
            485                 490                 495

Leu Asn Arg Arg Ala Asn Ala Leu Leu Ala Asn Gly Val Glu Leu Arg
            500                 505                 510

Asp Asn Gln Leu Val Val Pro Ser Glu Gly Leu Tyr Leu Ile Tyr Ser
            515                 520                 525

Gln Val Leu Phe Lys Gly Gln Gly Cys Pro Ser Thr His Val Leu Leu
530                 535                 540

Thr His Thr Ile Ser Arg Ile Ala Val Ser Tyr Gln Thr Lys Val Asn
545                 550                 555                 560

Leu Leu Ser Ala Ile Lys Ser Pro Cys Gln Arg Glu Thr Pro Glu Gly
            565                 570                 575

Ala Glu Ala Lys Pro Trp Tyr Glu Pro Ile Tyr Leu Gly Gly Val Phe
            580                 585                 590

Gln Leu Glu Lys Gly Asp Arg Leu Ser Ala Glu Ile Asn Arg Pro Asp
            595                 600                 605

Tyr Leu Asp Phe Ala Glu Ser Gly Gln Val Tyr Phe Gly Ile Ile Ala
            610                 615                 620

Leu
625

<210> SEQ ID NO 3
<211> LENGTH: 705
<212> TYPE: DNA
<213> ORGANISM: Artificial
<220> FEATURE:
<223> OTHER INFORMATION: Amino acid sequence of Trastuzumab's heavy
      chain-TNF alpha

<400> SEQUENCE: 3
atgcgtgtgc ctgctcagct gctgggtctg ctgctgctgt ggctgcgtgg ggctcgttgt    60
gacattcaga tgactcagtc tccttcatca ctgtccgcta gcgtgggcga cagagtcact   120

| | | |
|---|---|---|
| atcacctgcc gcgcatccca ggatgtgaac accgcagtcg cctggtatca gcagaagcct | 180 | |
| ggcaaagctc caaagctgct gatctactct gcaagtttcc tgtatagtgg agtgccctca | 240 | |
| aggttttcag ggtcccggag cggcaccgac ttcacactga ctatctccag cctgcagcct | 300 | |
| gaggattttg ccacatacta ttgccagcag cactatacca cccccctac tttcggccag | 360 | |
| ggaaccaaag tggagatcaa gcgaactgtg gccgctccat ctgtcttcat tttccaccc | 420 | |
| agtgacgaac agctgaagtc cgggacagct agcgtggtct gtctgctgaa caattttac | 480 | |
| cccagggaag ccaaagtgca gtggaaggtc gataacgctc tgcagtctgg aaatagtcag | 540 | |
| gagtcagtga cagaacagga ctccaaagat agcacttatt ctctgtctag taccctgaca | 600 | |
| ctgagcaagg cagactacga aagcataaa gtgtatgcct gtgaagtcac tcatcagggg | 660 | |
| ctgtccagtc ccgtcacaaa atcctttaat cgtggcgaat gttga | 705 | |

<210> SEQ ID NO 4
<211> LENGTH: 234
<212> TYPE: PRT
<213> ORGANISM: Artificial
<220> FEATURE:
<223> OTHER INFORMATION: Amino acid sequence of Trastuzumab's light
      chain

<400> SEQUENCE: 4

Met Arg Val Pro Ala Gln Leu Leu Gly Leu Leu Leu Leu Trp Leu Arg
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 5
<211> LENGTH: 18

<212> TYPE: DNA
<213> ORGANISM: Artificial
<220> FEATURE:
<223> OTHER INFORMATION: Primer M13-F

<400> SEQUENCE: 5
tgtaaaacga cggccagt                                                    18

<210> SEQ ID NO 6
<211> LENGTH: 20
<212> TYPE: DNA
<213> ORGANISM: Artificial
<220> FEATURE:
<223> OTHER INFORMATION: Primer KDP004

<400> SEQUENCE: 6
tcctggggac agtgacagtg                                                  20

<210> SEQ ID NO 7
<211> LENGTH: 41
<212> TYPE: DNA
<213> ORGANISM: Artificial
<220> FEATURE:
<223> OTHER INFORMATION: Primer KDP045

<400> SEQUENCE: 7
cactgtcact gtccccagga gtcagatcat cttctcgaac c                          41

<210> SEQ ID NO 8
<211> LENGTH: 22
<212> TYPE: DNA
<213> ORGANISM: Artificial
<220> FEATURE:
<223> OTHER INFORMATION: Primer TNF-R

<400> SEQUENCE: 8
aactagaagg cacagtcgag gc                                               22

<210> SEQ ID NO 9
<211> LENGTH: 18
<212> TYPE: DNA
<213> ORGANISM: Artificial
<220> FEATURE:
<223> OTHER INFORMATION: Primer M13-R

<400> SEQUENCE: 9
caggaaacag ctatgacc                                                    18

<210> SEQ ID NO 10
<211> LENGTH: 41
<212> TYPE: DNA
<213> ORGANISM: Artificial
<220> FEATURE:
<223> OTHER INFORMATION: Primer KDP077

<400> SEQUENCE: 10
gctaggcccc tttgttgatg cggcggacac ggtcacgagg g                          41

<210> SEQ ID NO 11
<211> LENGTH: 21
<212> TYPE: DNA
<213> ORGANISM: Artificial
<220> FEATURE:
<223> OTHER INFORMATION: Primer KDP020

<400> SEQUENCE: 11

```
gcatcaacaa aggggcctag c                                              21

<210> SEQ ID NO 12
<211> LENGTH: 22
<212> TYPE: DNA
<213> ORGANISM: Artificial
<220> FEATURE:
<223> OTHER INFORMATION: Primer BGH-R

<400> SEQUENCE: 12
aactagaagg cacagtcgag gc                                             22

<210> SEQ ID NO 13
<211> LENGTH: 19
<212> TYPE: DNA
<213> ORGANISM: Artificial
<220> FEATURE:
<223> OTHER INFORMATION: Primer KDP092

<400> SEQUENCE: 13
atggaacgcg gccgccacc                                                 19

<210> SEQ ID NO 14
<211> LENGTH: 19
<212> TYPE: DNA
<213> ORGANISM: Artificial
<220> FEATURE:
<223> OTHER INFORMATION: Primer KDP093

<400> SEQUENCE: 14
tctagcattt aggtgacac                                                 19

<210> SEQ ID NO 15
<211> LENGTH: 21
<212> TYPE: DNA
<213> ORGANISM: Artificial
<220> FEATURE:
<223> OTHER INFORMATION: Primer CMV-P

<400> SEQUENCE: 15
cgcaaatggg cggtaggcgt g                                              21

<210> SEQ ID NO 16
<211> LENGTH: 18
<212> TYPE: DNA
<213> ORGANISM: Artificial
<220> FEATURE:
<223> OTHER INFORMATION: Primer KDP033

<400> SEQUENCE: 16
agcttggtac cctcgagg                                                  18

<210> SEQ ID NO 17
<211> LENGTH: 45
<212> TYPE: DNA
<213> ORGANISM: Artificial
<220> FEATURE:
<223> OTHER INFORMATION: Primer KDP094

<400> SEQUENCE: 17
gacagatgga gcggccacag ttcgcttcag ctccagcttt gttcc                    45

<210> SEQ ID NO 18
<211> LENGTH: 21
<212> TYPE: DNA
<213> ORGANISM: Artificial
```

<220> FEATURE:
<223> OTHER INFORMATION: Primer KDP010

<400> SEQUENCE: 18
actgtggccg ctccatctgt c                                              21

<210> SEQ ID NO 19
<211> LENGTH: 1866
<212> TYPE: DNA
<213> ORGANISM: Artificial
<220> FEATURE:
<223> OTHER INFORMATION: Sequence encoding Cetuximab's heavy chain-TNF
      alpha

<400> SEQUENCE: 19
atgggctggt cctgcatcat cctgtttctg gtggccacag ccaccggcca ggtgcaactg      60
aagcagtccg gacctggcct ggtgcagcct tcccagtccc tgtccatcac ctgcaccgtg     120
tccggcttca gcctgaccaa ctacggagtg cactgggtga ggcagtcccc tggaaagggc     180
ctggaatggc tgggcgtgat ctggtccggc ggcaacaccg actacaacac ccccttcacc     240
tccaggctgt ccatcaacaa ggacaactcc aagtcccagg tcttcttcaa gatgaacagc     300
ctgcagtcca tgacaccgc catctattac tgcgccaggg ccctgaccta ctacgactac     360
gagttcgcct actggggaca gggaaccctc gtgaccgtgt ccgccgcatc aacaaagggg     420
ccttccgtgt ttccactggc ccctctagt aaaagcacct ctggcggaac agcagccctg     480
ggttgtctgg tgaaggacta cttcccagag ccagtcaccg tgtcctggaa cagcggcgcc     540
ctgacatccg gagtccatac ttttcctgct gtgctgcagt catccgggct gtacagcctg     600
agctctgtgg tcactgtccc aagttcatcc ctgggtactc agacctatat ctgcaacgtg     660
aatcacaagc catccaatac caaagtggac aagaaagtgg agcccaagag ctgtgataaa     720
acacatactt gcccccttg tcctgcacca gaactgctgg gaggtccatc cgtgttcctg     780
tttccaccca gcctaaaga caccctgatg atttctcgaa ctccagaggt cacctgcgtg     840
gtcgtggacg tgtcccacga ggaccccgaa gtcaagttca actggtacgt ggatggcgtc     900
gaagtgcata atgctaagac aaaaccaaga gaggaacagt acaacagcac ttatcgcgtc     960
gtgtctgtcc tgaccgtgct gcaccaggat tggctgaacg gcaaggagta aagtgcaaa    1020 gtgagcaata aggctctgcc cgcacctatc gagaaaacaa tttctaaggc taaaggacag    1080
cctagggaac cacaggtgta cactctgcct ccatctcggg aggaaatgac caagaaccag    1140
gtcagtctga catgtctggt gaaaggcttc tatccctccg acatcgcagt ggagtgggaa    1200
agcaatggac agcctgagaa caattacaag accacacccc ctgtgctgga ctctgatggc    1260
agtttctttc tgtatagtaa gctgaccgtg gataaatcac ggtggcagca gggaaatgtc    1320
tttagttgtt cagtgatgca cgaagcactg cacaatcact acactcagaa atcactgtca    1380
ctgtccccag gagtcagatc atcttctcga accccgagtg acaagcctgt agcccatgtt    1440
gtagcaaacc ctcaagctga ggggcagctc cagtggctga accgcgggc caatgccctc    1500 ctggccaatg gcgtggagct gagagataac cagctggtgg tgccatcaga gggcctgtac    1560
ctcatctact cccaggtcct cttcaagggc caaggctgcc cctccacca tgtgctcctc    1620 acccacacca tcagccgcat cgccgtctcc taccagacca aggtcaacct cctctctgcc    1680
atcaagagcc cctgccagag ggagacccca gagggggctg aggccaagcc ctggtatgag    1740
cccatctatc tgggagggt cttccagctg agaaggggtg accgactcag cgctgagatc    1800
aatcggcccg actatctcga ctttgccgag tctgggcagg tctactttgg gatcattgcc    1860
ctgtga                                                            1866

<210> SEQ ID NO 20
<211> LENGTH: 621
<212> TYPE: PRT
<213> ORGANISM: Artificial
<220> FEATURE:
<223> OTHER INFORMATION: Amino acid sequence of Cetuximab's heavy chain-
      TNF alpha

<400> SEQUENCE: 20

Met Gly Trp Ser Cys Ile Ile Leu Phe Leu Val Ala Thr Ala Thr Gly
1               5                   10                  15

Gln Val Gln Leu Lys Gln Ser Gly Pro Gly Leu Val Gln Pro Ser Gln
            20                  25                  30

Ser Leu Ser Ile Thr Cys Thr Val Ser Gly Phe Ser Leu Thr Asn Tyr
        35                  40                  45

Gly Val His Trp Val Arg Gln Ser Pro Gly Lys Gly Leu Glu Trp Leu
    50                  55                  60

Gly Val Ile Trp Ser Gly Gly Asn Thr Asp Tyr Asn Thr Pro Phe Thr
65                  70                  75                  80

Ser Arg Leu Ser Ile Asn Lys Asp Asn Ser Lys Ser Gln Val Phe Phe
                85                  90                  95

Lys Met Asn Ser Leu Gln Ser Asn Asp Thr Ala Ile Tyr Tyr Cys Ala
            100                 105                 110

Arg Ala Leu Thr Tyr Tyr Asp Tyr Glu Phe Ala Tyr Trp Gly Gln Gly
        115                 120                 125

Thr Leu Val Thr Val Ser Ala Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365
Leu Pro Pro Ser Arg Glu Glu Met Thr Lys Asn Gln Val Ser Leu Thr
        370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
                420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
        450                 455                 460
Val Arg Ser Ser Ser Arg Thr Pro Ser Asp Lys Pro Val Ala His Val
465                 470                 475                 480
Val Ala Asn Pro Gln Ala Glu Gly Gln Leu Gln Trp Leu Asn Arg Arg
                485                 490                 495
Ala Asn Ala Leu Leu Ala Asn Gly Val Glu Leu Arg Asp Asn Gln Leu
                500                 505                 510
Val Val Pro Ser Glu Gly Leu Tyr Leu Ile Tyr Ser Gln Val Leu Phe
        515                 520                 525
Lys Gly Gln Gly Cys Pro Ser Thr His Val Leu Leu Thr His Thr Ile
        530                 535                 540
Ser Arg Ile Ala Val Ser Tyr Gln Thr Lys Val Asn Leu Leu Ser Ala
545                 550                 555                 560
Ile Lys Ser Pro Cys Gln Arg Glu Thr Pro Glu Gly Ala Glu Ala Lys
                565                 570                 575
Pro Trp Tyr Glu Pro Ile Tyr Leu Gly Gly Val Phe Gln Leu Glu Lys
                580                 585                 590
Gly Asp Arg Leu Ser Ala Glu Ile Asn Arg Pro Asp Tyr Leu Asp Phe
        595                 600                 605
Ala Glu Ser Gly Gln Val Tyr Phe Gly Ile Ile Ala Leu
        610                 615                 620

<210> SEQ ID NO 21
<211> LENGTH: 693
<212> TYPE: DNA
<213> ORGANISM: Artificial
<220> FEATURE:
<223> OTHER INFORMATION: Sequence encoding Cetuximab's light chain

<400> SEQUENCE: 21

```
atgggctggt cctgcatcat cctgttcctg gtggccacag ccaccggcga catcctgctg      60
acccagtccc ctgtgattct gagcgtctcc cccggcgaaa gggtgtcctt cagctgcagg     120
gccagccagt ccatcggcac caacatccac tggtaccagc agaggaccaa tggctccccc     180
aggctgctca tcaagtacgc ctccgagtcc atctccggca tcccctccag gttctccgga     240
tccggatccg gcaccgactt caccctgtcc atcaactccg tggagtccga ggacatcgcc     300
gactactact gccagcagaa caacaactgg cccaccacct cggcgccgg aacaaagctg      360
gagctgaagc gaactgtggc cgctccatct gtcttcattt tccacccag tgacgaacag      420
ctgaagtccg gacagctag cgtggtctgt ctgctgaaca attttacccc cagggaagcc     480
aaagtgcagt ggaaggtcga taacgctctg cagtctggaa atagtcagga gtcagtgaca     540
```

```
gaacaggact ccaaagatag cacttattct ctgtctagta ccctgacact gagcaaggca    600
gactacgaga agcataaagt gtatgcctgt gaagtcactc atcaggggct gtccagtccc    660
gtcacaaaat cctttaatcg tggcgaatgt tga                                 693
```

<210> SEQ ID NO 22
<211> LENGTH: 230
<212> TYPE: PRT
<213> ORGANISM: Artificial
<220> FEATURE:
<223> OTHER INFORMATION: Amino acid sequence of Cetuximab's light chain

<400> SEQUENCE: 22

```
Met Gly Trp Ser Cys Ile Ile Leu Phe Leu Val Ala Thr Ala Thr Gly
1               5                   10                  15

Asp Ile Leu Leu Thr Gln Ser Pro Val Ile Leu Ser Val Ser Pro Gly
            20                  25                  30

Glu Arg Val Ser Phe Ser Cys Arg Ala Ser Gln Ser Ile Gly Thr Asn
        35                  40                  45

Ile His Trp Tyr Gln Gln Arg Thr Asn Gly Ser Pro Arg Leu Leu Ile
    50                  55                  60

Lys Tyr Ala Ser Glu Ser Ile Ser Gly Ile Pro Ser Arg Phe Ser Gly
65                  70                  75                  80

Ser Gly Ser Gly Thr Asp Phe Thr Leu Ser Ile Asn Ser Val Glu Ser
                85                  90                  95

Glu Asp Ile Ala Asp Tyr Tyr Cys Gln Gln Asn Asn Asn Trp Pro Thr
            100                 105                 110

Thr Phe Gly Ala Gly Thr Lys Leu Glu Leu Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys
225                 230
```

ANTIBODY-TNF α FUSION PROTEIN AND ITS PREPARATION AND APPLICATIONS

FIELD OF THE INVENTION

The present invention belongs to the fields of biotechnology and medicine. Specifically, the present invention relates to an antibody based targeted tumor immunotherapy, wherein an antibody against a tumor antigen is conjugated with the tumor necrosis factor α (TNFα) having the activities of tumor killing and activating antitumor immunity to construct an antibody-TNFα fusion protein using technology of molecular cloning.

BACKGROUND

TNFα is a pleiotropic cytokine having a wide range of biological activities and immunoregulatory activities. It is known as capable of inhibiting murine and human tumor cells in mice. Therefore, it has been widely studied as a potential anti-tumor agent (N J Roberts et al., Systemic use of tumor necrosis factor alpha as an anticancer agent, Oncotarget, 2 (10): 739-51, 2011).

TNFα suppresses tumor development mainly by directly killing tumor cells and inducing necrosis or apoptosis in tumor cells. In addition, TNFα, as a costimulatory molecule for T cell proliferation, can enhance immune response, induce expression of type I and type II MHC antigens on macrophages and induce secretion of TNFα, IFNs and IL-1 (Balkwill F., "Tumor necrosis factor. Improving on the formula.", Nature, 361 (6409): 206-7,1993).

Unfortunately, systemic administration of TNFα to human patients was associated to strong pro-inflammatory response, which caused intolerable toxicity before reaching the therapeutic effective threshold (K J. Tracey and A. Cerami, Tumor necrosis factor, other cytokines and disease. Ann. Rev. Cell Biol, 9:317-43, 1993). Furthermore, TNFα has a short half-life in vivo inherently. Thereby, clinical applications of TNFα in treating tumors are limited.

In exploration for solutions, methods were developed to reduce toxicity of TNFα. In one instance, the TNFα molecule was conjugated to a Fab or Fv fragment of an antibody specific to a tumor antigen, whereby the TNFα molecule was directed to the site of tumor (H R Hoogenboom et al., Construction and expression of antibody-tumor necrosis factor fusion proteins, Mol. Immunol., 28: 1027-37, 1991). Therein, a peptide linker was used between the antibody moiety and the TNFα moiety. In another instance, TNFα was conjugate to a mini-peptide that is specific to tumor angiogenesis, whereby TNFα destroys the vessels of tumor angiogenesis, without impacting on other tissues (P. Matteo et al., Anti-metastatic tumor activity of the vascular targeting agent of the NGR-TNF, Clin. Exp. Metastasis, 32 (3): 289-300, 2015). In a further instance, the TNFα molecule was modified at several positions along its amino acid sequence to reduce toxicity without influencing its anti-tumor activity (H. Loetscher et al, Human tumor necrosis factor alpha (TNF alpha) mutants with exclusive specificity for the 55-kDa or 75 kDa TNF receptors, J. Biol. Chem., 268:26350-7, 1993). Although these methods have made some progress in clinical trials, none have been approved for clinical use. Therefore, there remains the need for approaches to specifically enhance the anti-tumor toxicity of TNFα or to make tumor cells more sensitive to the toxicity of TNFα in combination with by some other agent, to thereby prevent normal tissues from being damaged by the toxicity of TNFα.

Many tumor cells overexpress receptors of cell growth factors, such as members of the ErbB family, like EGFR and Her-2. These proteins are taken as targets of oncotherapy in clinic. Antibodies against these targets were used for binding to surface of tumor cells to induce antibody-dependent cell-mediated cytotoxicity (ADCC) and/or complement dependent cytotoxicity (CDC) or to block the signal pathways involved in tumor cell growth and/or metastasis to kill tumors (J. Baselga, C L. Arteaga, Critical update and emerging trends in epidermal growth factor receptor targeting in cancer, J. Clin. Oncol., 23 (11):2445-59 2005; C A. Hudis, Trastuzumab-mechanism of action and use in clinical practice, New Eng. J. Med., 357:39-51, 2007).

There exists the persistent need for anti-tumor drugs and treatments with improved targeting property, enhanced efficacy and decreased toxicity. This application provides solutions.

SUMMARY OF THE INVENTION

Herein below is summary of the invention.

In one aspect, the present invention provides a fusion protein of an antibody and TNFα, comprising an antibody moiety and a TNFα moiety conjugated to the C-terminal of the heavy chain of said antibody, whereby said fusion protein comprises a heavy chain comprising the heavy chain of said antibody with said TNFα moiety linked at the C-terminal optionally through a peptide linker and optionally a signal peptide at N-terminal, and a light chain comprising the light chain of said antibody and optionally a signal peptide at N-terminal;

Wherein, said antibody is specific to a tumor antigen; and wherein, said TNFα moiety is selected from the group consisting of TNFα and a functionally equivalent analog or derivative thereof.

In another aspect, the present invention provides a nucleic acid construct, comprising or consisting of a nucleic acid molecule encoding the heavy chain of the fusion protein of the invention and/or a complement of said nucleic acid molecule. The nucleic acid construct may be a vector, such as an expression vector.

In another aspect, the present invention provides a nucleic acid construct or a combination of nucleic acid constructs, comprising or consisting of a nucleic acid molecule encoding the heavy chain of the fusion protein of the invention and a nucleic acid molecule encoding the light chain of the fusion protein, and/or complements of said nucleic acid molecules. The nucleic acid molecule encoding the heavy chain of the fusion protein and/or the complement thereof and the nucleic acid molecule encoding the light chain and/or the complements thereof may be included in the same nucleic acid construct or in two or more nucleic acid constructs. Said nucleic acid construct may be a vector, such as an expression vector.

In another aspect, the present invention provides a host cell comprising the nucleic acid construct or combination of nucleic acid constructs of the invention, such as a vector or a combination of vectors.

In another aspect, the present invention provides a method for producing the fusion protein of the invention, including: culturing the host cell of the invention under a condition suitable for expression of the fusion protein to express the fusion protein; isolating the fusion protein; and optionally one or more of the following steps: subjecting culture of the host cell to a stress to obtain a strain having a high expression of the fusion protein, such as culturing under the stress of methotrexate, preferably an increasing gradient of methotrexate stress; and separating and/or purifying the fusion protein.

In another aspect, the present invention provides a composition comprising the fusion protein, the nucleic acid construct, the combination of nucleic acid constructs and/or the host cell of the invention. The composition may optionally further comprise one or more additional active agents for treating or for preventing tumors.

In another aspect, the present invention provides use of the fusion protein, the nucleic acid construct, the combination of nucleic acid constructs, the host cell and the composition of the invention for manufacturing a product for inducing apoptosis in tumor cells, inhibiting growth of tumor and/or treating a tumor. Optionally, the product may further comprise one or more additional active agents for treating or for preventing tumors.

In another aspect, the present invention provides a method for inducing apoptosis in tumor cells and/or inhibiting growth of tumor and/or treating a tumor, wherein said method comprises administering to a subject in need thereof a therapeutically effective amount of the fusion protein, the nucleic acid construct, the combination of nucleic acid constructs, the host cell or the composition of the invention. Optionally, the method may further comprise administration of one or more additional active agents for treating and/or for preventing tumors simultaneously with, before or after administration of the fusion protein, the nucleic acid construct, the combination of nucleic acid constructs, the host cell or the composition of the invention.

In another aspect, the present invention provides the fusion protein, the nucleic acid construct, the combination of nucleic acid constructs, the host cell or the composition of the invention for use as a medicine. In another aspect, the present invention provides the fusion protein, the nucleic acid construct, the combination of nucleic acid constructs, the host cell or the composition of the invention for inducing apoptosis in tumor cells, inhibiting growth of tumor and/or treating a tumor. The use may combine with one or more additional active agents for treating and/or for preventing tumors.

BRIEF DESCRIPTION OF THE DRAWINGS

The drawings are provided for purpose of illustration and exemplification, with no effect of limiting the scope of the invention.

FIG. 1: Schematic depiction of an embodiment of the antibody-TNFα fusion protein according to the present invention.

FIGS. 2A-2C: SDS-PAGE electrophoresis and HPLC-SEC of Trastuzumab-TNFα fusion protein. The antibody-TNFα fusion protein was purified via Protein-A affinity chromatography followed by an anion exchange chromatography to collect the flow-through. FIG. 2A: 6% non-reducing SDS-PAGE electrophoresis, 3 μg each sample; lane 1: the Trastuzumab-TNFα fusion protein, lane 2: Trastuzumab. FIG. 2B: 10% reducing SDS-PAGE electrophoresis, 5 μg each sample; lane 1: the Trastuzumab-TNFα fusion protein, lane 2: Trastuzumab, the rightmost lane: the protein molecular weight ladder (kDa). FIG. 2C: HPLC-SEC of the Trastuzumab-TNFα fusion protein using TSKgel G3000SWXL, wherein, the line starting atop represents the protein molecular weight ladder, the line starting in the middle represents Trastuzumab, and the line lowest represents the antibody-TNFα fusion protein.

FIGS. 3A-3C: SDS-PAGE electrophoresis and HPLC-SEC of Cetuximab-TNFα fusion protein. The antibody-TNFα fusion protein was purified via Protein-A affinity chromatography followed by an anion exchange chromatography to collect the flow-through. FIG. 3A: 6% non-reducing SDS-PAGE electrophoresis, 3 μg each sample; lane 1: the Cetuximab-TNFα fusion protein, lane 2: human IgG1. FIG. 3B: 10% reducing SDS-PAGE electrophoresis, 5 μg each sample; lane 1: the Cetuximab-TNFα fusion protein, lane 2: human IgG1. FIG. 3C: HPLC-SEC of the Cetuximab-TNFα fusion protein using TSKgel G3000SWXL, wherein, the line starting atop represents the protein molecular weight ladder, the line starting in the middle represents the Cetuximab-TNFα fusion protein, and the line lowest represents human IgG1.

FIG. 4A: ELISA of binding to Her-2 ECD in vitro. A 96-well ELISA plate was coated with 25 nM recombinant human Her-2 ECD, and the antibody bound to Her-2 ECD was detected using alkaline phosphatase-labeled goat anti-human IgG1 Fc antibody. FIG. 4B: Flow cytometry of the antibody-TNFα fusion protein's binding to Her-2 on cell surface. Three Her-2 positive human tumor cell lines (PANC-1, SKBR-3 and SKOV-3) were incubated with the antibody-TNFα fusion protein at different concentrations (Y-axis); the antibody bound to Her-2 ECD was detected using FITC-labeled goat anti-human IgG1 Fc antibody, and the FITC fluorescence intensity was detected on a flow cytometer. Mock is the group without the antibodies.

FIG. 7A: the NCI-N87 cells were incubated with the antibody-TNFα fusion protein at different concentrations for 1 day; and cell survival was detected using a CCK-8 kit. FIG. 7B: the NCI-N87 cells were incubated with 10 ng/ml Trastuzumab-TNFα fusion protein, a mixture of 10 ng/ml Trastuzumab and 2 ng/ml of TNFα, or 2 ng/ml of TNFα for 1 day, respectively; and cell survival was detected using a CCK-8 kit. FIG. 7C: a picture of apoptosis induced by the antibody-TNFα fusion protein in NCI-N87 cells under microscopy (40×).

FIG. 9A: Her-2 positive human tumor cells (NCI-N87, SKBR-3 and SKOV-3) were cultured in the presence of the fusion protein, actinomycin D or both for 1 day; and cell viability was detected using a CCK-8 kit. FIG. 9B: Her-2 positive human tumor cells (BT-474, NCI-N87, SKBR-3 and SKOV-3) were cultured in the presence of the fusion protein, doxorubicin or both for 1 day; and cell viability was detected using a CCK-8 kit.

FIG. 10A: Mouse forestomach carcinoma (MFC) cells stably expressing human Her-2 and wild-type MFC cells cultured in presence of 5 μg/ml CHX were treated with the Trastuzumab-TNFα fusion protein at different concentrations or a mixture of Trastuzumab and TNFα for 20 hours, and cell viability was detected using a CCK-8 kit. FIG. 10B: Mouse forestomach carcinoma (MFC) cells stably expressing human Her-2 and wild-type MFC cells cultured in presence of 5 μg/ml CHX were treated with the Trastuzumab-TNFα fusion protein at different concentrations for 20 hours, and cell viability was detected using a CCK-8 kit. FIG. 10C: Mouse forestomach carcinoma (MFC) cells stably expressing human Her-2 and wild-type MFC cells cultured in presence of 5 μg/ml ActD were treated with the Trastuzumab-TNFα fusion protein at different concentrations for 20 hours, and cell viability was detected using a CCK-8 kit. FIG. 10D: Mouse forestomach carcinoma (MFC) cells stably expressing human Her-2 cultured in presence of 5 μg/ml ActD were treated with the Trastuzumab-TNFα fusion protein at different concentrations or a mixture of Trastuzumab and TNFα for 20 hours, and cell viability was detected using a CCK-8 kit.

FIG. 14A: Balb/c mice were grafted with the CT26 tumor cells expressing human Her-2 on back. The mice were treated via caudal intravenous injection. FIG. 14B: Balb/c mice were grafted with the CT26 tumor cells expressing human Her-2 on back. The mice were treated with 3 mg/kg Trastuzumab-TNFα fusion protein or 3 mg/kg mixture of the Trastuzumab and TNFα via caudal intravenous injection. Tumor volume was measured and calculated as (length×width×width/2).

DETAILED DESCRIPTION OF THE INVENTION

Figure 3A:
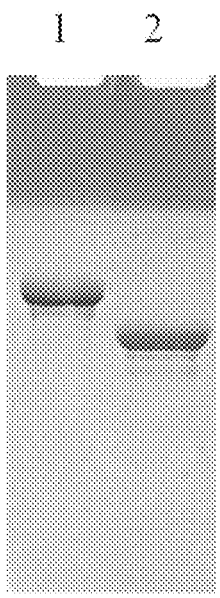

In the following, the present invention will be described in details with reference to specific embodiments.

This application is based on the finding that TNFα can be conjugated to an antibody molecule to provide a dual-target antibody-TNFα fusion protein which exhibits strong tumor-specific effects including inhibition, killing and apoptosis-induction in vitro and in vivo. Furthermore, these fusion proteins in combination with an additional anti-tumor active, such as a chemotherapeutic agent, provide an effect of synergism in killing, inhibition and apoptosis-induction in tumor cells in vitro and in vivo.

The inventors designed and produced an antibody-TNFα fusion protein with multiple biological activities. Specifically, the inventors, using the technology of molecular cloning, constructed an antibody-TNFα fusion protein by conjugating an antibody against a tumor-specific molecule on cell surface or a molecule over-expressed by tumor cells (e.g. tumor-specific antigens and tumor-associated antigens) with tumor necrosis factor α (TNFα) which is capable of tumor-killing and activation of anti-tumor immunity. The antibody moiety recruits the fusion protein to the environment around the tumor cells, producing actions on the tumor cells including inhibition, killing and induced apoptosis. The fusion protein carries the TNFα molecule as conjugated with the antibody to the site of tumor, where the TNFα molecule forms a transmembrane format with the tumor-specific molecule on surface and kills the tumor cells. Further, in presence of an active agent that is cytotoxic to tumor (e.g., a chemotherapeutic agent), the antibody-TNFα fusion protein of the invention and the active agent provide an enhancement of synergism in killing tumor cells.

The invention has overcome various technical obstacles, including difficulties in recombinant protein expression, difficulties in obtaining a productive strain with high expression of the product, and the risk that the expressed recombinant protein fails to fold into the correct configuration and is thus insoluble or prone to aggregate or biologically inactive, and succeeded in a recombinant protein molecule that can be effectively expressed in mammalian cells.

The fusion protein of the invention is stable in expression, highly biologically active and is effective in treating and preventing tumors. For example, the fusion protein of the invention can effectively inhibit osteogenic and cartilage differentiation, and can be effectively used for treating cancers, such as gastric cancer, pancreatic cancer, breast cancer, ovarian cancer, melanoma and colon cancer. The fusion protein of the invention can also be used in combination with an additional anti-tumor agent to provide a synergistic anti-tumor effect.

As used herein, the open-ended terms such as "comprise", "have" and "include" and their grammatical variants encompass the scenarios as meant by the closed-ended terms such as "consist of . . . ", "composed of . . . " and "is . . . ". In the present application, a numerical range constitutes a disclosure including the values at two ends, every integer and fractions between the ends, and all ranges formed between values of said ends, integers and fractions. For multiple ranges described for a single parameter, ends of these ranges can be recombined the new ranges obtained thereby are also deemed as specifically disclosed herein. In the present application, the features and elements can be recombined across embodiments and examples and the embodiments and examples obtained thereby are also deemed as specifically disclosed herein.

Fusion Protein and its Components

The fusion proteins of the invention is a fusion protein between an antibody and TNFα, which is also referred to herein below as "antibody-TNFα fusion protein" or "antibody-TNFα" or "the fusion protein of the invention", as well as synonyms in context. The fusion protein of the invention comprises an antibody moiety and a TNFα moiety conjugated to the C-terminal of the heavy chain of said antibody, wherein the heavy chain of the antibody and the TNFα moiety are fused to form the heavy chain of the fusion protein, and the light chain of the antibody constitutes the light chain of the fusion protein. The heavy chain and the light chain of the fusion protein each may independently and optionally further comprise a signal peptide at N-terminal.

In a preferred embodiment, the antibody moiety in the fusion protein of the invention is in the form of a full-length antibody. The form of a full-length antibody refers to the complete structure of an immunoglobulin (Ig), except for optional C-terminal modification to facilitate fusion. In particular, the structure of an immunoglobulin refers to the structure of a monomeric Ig molecule such as IgG. In context of the present invention, immunoglobulins include IgG, IgD, IgE, IgA, IgM and sub-classifications and subunits thereof. For example, according to the present invention, the antibody may be an IgG antibody, including those of IgG1, IgG2, IgG3, and IgG4 sub-classes. In a preferred embodiment, as shown in FIG. 1, the TNFα molecule is connected to the C-terminal of the Fc fragment of the full-length antibody.

In the fusion protein of the invention, the antibody moiety provides specificity to a tumor antigen. Examples of tumor antigen include, but are not limited to, members of the ErbB family, such as EGFR, Her-2, Her-3, and Her-4. Correspondingly, the antibodies include EGFR antibodies, Her-2 antibodies, Her-3 antibodies and Her-4 antibodies. Specifically, examples of antibody include, but are not limited to Trastuzumab, Pertuzumab (Perjeta), T-DM1, Cetuximab, ABX-EGF, and functionally equivalent analogs or derivatives thereof.

As used herein, the term "functionally equivalent analog or derivative" should be understood in a broad sense as referring to an agent that is highly similar to a specified biomolecule as reference (such as a cellular element, a nucleic acid molecule, a cytokine (e.g., TNFα)) in structure and/or composition or that comprises the backbone structure of the reference and has no significant difference in biological activity as compared with the reference. For example, in the context of nucleic acid molecules and proteins such as antibodies, functionally equivalent analogs or derivatives thereof include molecules that are different from the reference molecule at one or more positions along the nucleotide sequence or the amino acid sequence via mutation of deletion, insertions and/or substitution while having a sequence identity of at least 60%, 70%, 80%, 90%, 95%, 97%, 98%, or even at least 99% to the reference. For example, in the context of TNFα, the functionally equivalent analogs or derivatives thereof have substantially the same or equivalent effect in killing cells and inducing apoptosis.

In some embodiments, the antibody is a Her-2 antibody or an EGFR antibody. In some embodiments, the antibody is a Her-2 antibody, such as Trastuzumab or a functionally equivalent analog or derivative thereof. In some embodiments, the antibody is Trastuzumab.

In some embodiments, the antibody is an EGFR antibody, such as Cetuximab or a functional analog or derivative thereof. In some embodiments, the antibody is Cetuximab.

In some embodiments, the antibody molecule comprises C-terminal modification to facilitate fusion, such as deletion of one or more lysine residues at C-terminal of the heavy chain. For example, the antibody moiety derived from Trastuzumab or Cetuximab may comprise the lysine deletion at C-terminal.

In the fusion protein of the invention, the TNFα moiety refers to monomeric molecule(s) of TNFα or a functionally equivalent analog or derivative thereof. In some embodiments, the TNFα molecule is selected from: human or mammalian TNFα; mature TNFα, secreted TNFα, and transmembrane TNFα. In some embodiments, the TNFα moiety is a human TNFα. For example, in a fusion protein of the invention, the TNFα moiety has the amino acid sequence of positions 469-625 in SEQ ID NO: 2.

In a preferred embodiment, the TNFα moiety is directly conjugated to the C-terminal of the heavy chain of the antibody, without a peptide linker. Meanwhile, the TNFα portion can also be conjugated to the heavy chain of the antibody via a peptide linker. The peptide linker, if present, may have a length of 1-50, 5-50, 5-40, 10-40 or 10-30 amino acid residues, or a length of an integer from 1 to 50. A person of skills in the art knows how to determine the presence/absence and length of the peptide linker with conventional analysis and means, see for example PNAS, 95: 5929-5934, 1998; Protein Eng., 13 (5): 309-312, 2000; Protein Eng., 15 (11): 871-879, 2003; etc.

In a preferred embodiment, the antibody moiety is in the form of the tetramer of a monomeric Ig molecule, and the molar ratio of antibody to TNFα in the form of monomeric molecule(s) is 1:1 or preferably 1:2, as shown in FIG. 1.

In some embodiments, the fusion protein further comprises a signal peptide at N-terminal. As understood, a signal peptide refers to an amino acid sequence that functions to direct secretion, localization and/or transportation of proteins, which usually have a length of 5-30 amino acid residues. Generally, a mature protein harvested in recombinant production does not contain a signal peptide.

In an exemplary embodiment, the heavy chain of the fusion protein according to the present invention has the amino acid sequence of positions 20-625 (without signal peptide) or positions 1-625 (with signal peptide) in SEQ ID NO: 2, and the light chain of the fusion protein has the amino acid sequence of positions 21-234 (without signal peptide) or positions 1-234 (with signal peptide) in SEQ ID NO: 4. Along the amino acid sequence as set forth by SEQ ID NO: 2, the segment of amino acids (aa) at positions 1-19 is a transmembrane signal peptide, the segment of aa 20-468 is the heavy chain of Trastuzumab with the lysine-deletion at C-terminal, the segment of aa 469-625 is the amino acid sequence of human TNFα. Along the amino acid sequence as set forth by SEQ ID NO: 4, the segment of aa 1-20 is the transmembrane signal peptide, and the segment of aa 21-234 is the light chain of Trastuzumab. SEQ ID NO: 1 is an example of nucleotide sequence encoding the amino acid of SEQ ID NO: 2, wherein the last TGA is the stop codon. SEQ ID NO: 3 is an example of nucleotide sequence encoding SEQ ID NO: 4, wherein the last TGA is the stop codon.

In another exemplary embodiment, the heavy chain of the fusion protein according to the present invention has the amino acid sequence of positions 17-621 (without signal peptide) or positions 1-621 (with signal peptide) in SEQ ID NO: 20, and the light chain of the fusion protein has the amino acid sequence of positions 17-230 (without signal peptide) or positions 1-230 (with signal peptide) in SEQ ID NO: 22. Along the amino acid sequence as set forth by SEQ ID NO: 20, the segment of amino acids (aa) at positions 1-16 is the transmembrane signal peptide, the segment of aa 17-464 is the heavy chain of Cetuximab with the lysine-deletion at C-terminal, the segment of aa 465-621 is the amino acid sequence of human TNFα. Along the amino acid sequence as set forth by SEQ ID NO: 22, the segment of aa 1-16 is the transmembrane signal peptide, and the segment of aa 17-230 is the light chain of Cetuximab. SEQ ID NO: 19 is an example of nucleotide sequence encoding the amino acid of SEQ ID NO: 20, wherein the last TGA is the stop codon. SEQ ID NO: 21 is an example of nucleotide sequence encoding SEQ ID NO: 22, wherein the last TGA is the stop codon.

As shown by the examples in the present application, the fusion protein of the invention has one or more activities selected from the group consisting of binding to a tumor antigen, promoting apoptosis in fibroblasts, inducing apoptosis in tumor cells, inhibiting growth of tumor, and providing a synergistic anti-tumor effect in combination with an additional anti-tumor agent.

The Fusion Protein-Encoding Nucleic Acid Molecules, Nucleic Acid Constructs, Vectors and Host Cells As used herein, the term "nucleic acid construct" is chemically synonymous with "nucleic acid molecule", which is artificial in origin and is not a natural product. Therefore, a nucleic acid construct, as in the case of a nucleic acid molecule, may include another encoding nucleic acid molecule, i.e., a coding sequence, as an integral component thereof, such as is the case of a vector containing a coding sequence. As used herein, the terms "nucleic acid molecule", "nucleic acid" and "nucleotide sequence" in relation to an encoding sequence or a specified nucleotide sequence are interchangeably synonymous, all encompass the nucleic acid molecule or sequence that is complementary to a specified nucleic acid molecule or sequence.

Provided herein is a nucleic acid construct, comprising a nucleotide sequence encoding the heavy chain of the fusion protein of the invention, such as a vector comprising said nucleotide sequence. Or, the nucleic acid construct is a nucleic acid molecule encoding the heavy chain of the fusion protein of the invention.

In an embodiment, a nucleic acid construct according to the invention may be a nucleic acid molecule encoding the fusion protein heavy chain consisting of Trastuzumab heavy chain-human TNFα, or a construct such as a vector comprising said encoding nucleic acid molecule. For example, the nucleic acid construct may comprise or consist of a nucleic acid molecule selected from the followings:

A nucleic acid molecule encoding the amino acid sequence of aa 20-625 or aa 1-625 in SEQ ID NO: 2; or A nucleic acid molecule comprising the nucleotide sequence of positions 58-1875 or positions 1-1875 in SEQ ID NO: 1 and optionally a stop codon; or A nucleic acid molecule having the nucleotide sequence of SEQ ID NO: 1.

In another embodiment, a nucleic acid construct of the present invention may be a nucleic acid molecule encoding the fusion protein heavy chain consisting of Cetuximab heavy chain-human TNFα, or a construct such as a vector comprising said encoding nucleic acid molecule. Specifically, the nucleic acid construct may comprise or consist of a nucleic acid molecule selected from the followings:

A nucleic acid molecule encoding the amino acid sequence of positions 17-621 or positions 1-621 in SEQ ID NO: 20; or A nucleic acid molecule comprising the nucleotide sequence of positions 49-1863 or positions 1-1863 in SEQ ID NO: 19 and optionally a stop codon; or A nucleic acid molecule having the nucleotide sequence of SEQ ID NO: 19.

Also provided herein is a nucleic acid construct or a combination of nucleic acid constructs, comprising or consisting of a nucleic acid molecule encoding the heavy chain of the fusion protein of the invention and a nucleic acid molecule encoding the light chain of the fusion protein of the invention. The nucleic acid molecule encoding the heavy chain of the fusion protein and the nucleic acid molecule encoding the light chain of the fusion protein may be included in the same nucleic acid construct (e.g., a vector) or in two or more nucleic acid constructs (e.g., vectors).

For example, in some embodiments, when the fusion protein is Trastuzumab-TNFα, correspondingly, said nucleic acid construct or combination of nucleic acid constructs may comprise or consist of the following nucleic acid molecules:

A nucleic acid molecule encoding the amino acid sequence of positions 20-625 or positions 1-625 in SEQ ID NO: 2, and a nucleic acid molecule encoding the amino acid sequence of positions 21-234 or positions 1-234 in SEQ ID NO: 4; or A nucleic acid molecule comprising the nucleotide sequence of positions 58-1875 or positions 1-1875 in SEQ ID NO: 1 and optionally a stop codon, and a nucleic acid molecule comprising the nucleotide sequence of positions 61-702 or positions 1-702 in SEQ ID NO: 3 and optionally a stop codon; or A nucleic acid molecule having the nucleotide sequence of SEQ ID NO: 1 and a nucleic acid molecule having the nucleotide sequence of SEQ ID NO: 3.

In some other embodiments, when the fusion protein is Cetuximab-TNFα, correspondingly, said nucleic acid construct or combination of nucleic acid constructs may comprise or consist of the following nucleic acid molecules:

A nucleic acid molecule encoding the amino acid sequence of positions 17-621 or positions 1-621 in SEQ ID NO: 20, and a nucleic acid molecule encoding the amino acid sequence of positions 17-230 or positions 1-230 in SEQ ID NO: 22; or A nucleic acid molecule comprising the nucleotide sequence of positions 49-1863 or positions 1-1863 in SEQ ID NO: 19 and optionally a stop codon, and a nucleic acid molecule comprising the nucleotide sequence of positions 49-690 or positions 1-690 in SEQ ID NO: 21 and optionally a stop codon; or A nucleic acid molecule having the nucleotide sequence of SEQ ID NO: 19 and a nucleic acid molecule having the nucleotide sequence of SEQ ID NO: 21.

As said above, a nucleic acid construct may comprise or consist of a vector. Accordingly, the present invention also provides a vector comprising an encoding nucleic acid molecule according to the present invention. In some embodiments, the vector may be an expression vector, which provides expression of the fusion protein in a host cell. In the context of present application, the term "vector" includes, for example, expression vectors, cloning vectors, plasmids, cosmids and viral vectors. Representative examples include, but are not limited to, vectors providing expression in eukaryotic cells (e.g., CHO cells and COS cells), vectors providing expression in *Saccharomyces cerevisiae* or *Pichia pastoris* cells, vectors providing expression in insect (e.g., silkworm) cells, and prokaryotic expression vector. In the context of the present invention, any vectors known in the art, such as those commercially available ones, can be used. For example, a nucleotide sequence encoding the novel fusion protein of the invention can be cloned into a vector as operably conjugate to a regulatory sequence for expression to thereby form an expression vector for the fusion protein.

Also provided herein is a host cell which is transformed to comprise the nucleic acid construct or combination of nucleic acid constructs as described above. In the context of the present application, the term "host cell" includes prokaryotic cells and eukaryotic cells. In some embodiments, the host cell may be selected from the group consisting of bacteria, fungi, yeasts, plant cells and animal cells. Examples of commonly used prokaryotic host cells include, for example, *Escherichia coli* and *Bacillus subtilis*. Commonly used eukaryotic host cells include yeast cells, insect cells and mammalian cells. In some embodiments, the host cell is a mammalian cell, such as a CHO cell, for example, CHO DG44 and CHO-K. In the context of the present application, the term "transform" refers to introducing a nucleic acid of interest or a vector comprising same into a host cell by any of the methods of transformation known in the art, whereby the obtained host cell is not a natural product. Methods of transformation may be selected according to types of the given host, and generally include, for example, electrotransformation, transfection using calcium chloride, DEAE-dextran or other reagents, particle bombardment, lipofection and infection (see Sambrook et al. Molecular Cloning Laboratory Guide, 2nd edition, 1989). A preferred method may be electrotransformation.

The present invention also provides a method for producing an antibody-TNFα fusion protein, wherein the method may include: culturing a transformed host cell as described above under a condition suitable for expression of the fusion protein to express the fusion protein; and isolating the fusion protein. The method may further include a step of subjecting culture of the host cell to a stress to obtain a strain having a high expression of the fusion protein, such as culturing under the stress of methotrexate, preferably an increasing gradient of methotrexate stress. The method may further include one or more steps of separating and/or purifying the fusion protein. Determination on parameters of culturing, such as medium, temperature and time, is within the normal skills of a person of skills in the art. Expression of the fusion protein can be detected using any of the conventional means of detection, such as SDS-PAGE and Western blotting. For purifying the fusion protein, any of the conventional separation and purification techniques can be used, including centrifugation, precipitation, filtration and chromatography. Specifically, useful chromatography techniques include, for example, affinity chromatography, gel filtration, ion exchange, hydrophobic chromatography and reverse chromatography. Specific examples include Protein-A affinity chromatography (e.g., POROS MabCapture A, Life Tech) and anion exchange chromatography (e.g., Q-600C, TOSOH).

Composition

A composition according to the present invention may comprise an effective amount of an antibody-TNFα fusion protein, a nucleic acid construct, a combination of nucleic acid constructs and/or a host cells according to the present invention. The composition may be a pharmaceutical composition, which may comprise a pharmaceutically acceptable carrier such as a solvent, excipient and adjuvant. In the context of the present application, the term "an effective amount" or "an effective dosage" refers to an amount providing to a human or animal subject a function or activity as intended and being tolerable to the human or animal subject. As used herein, the term "pharmaceutically acceptable" means that when a molecular or a composition is administered to an animal or human subject in an appropriate manner or route, it does not produce an undesired effect (such as toxicity, irritation and allergy), as demonstrated by a reasonable benefit/risk ratio. The term "a pharmaceutically acceptable carrier" is supposed to be compatible with the fusion protein of the invention, which can normally be blended with the protein without causing significant loss in efficacy of the pharmaceutical composition. Specific examples of substances that can be used as a pharmaceutically acceptable carrier or ingredient can be found in, for example, Remington: The Science and Practice of Pharmacy (2005), the 21st Century Edition, Lippincott Williams and Wilkins, Philadelphia, PA.

The pharmaceutical compositions according to the present invention may be formulated into a dosage form as appropriate for a specific dosage or manner of administration.

A nucleic acid molecule may be delivered to a subject in the form of a naked nucleic acid molecule, a co-delivery preparation or a recombinant vector (e.g., a plasmids or a viral vector) comprising and/or expressing the nucleic acid molecule. Suitable delivery reagents for administration include the lipophilic reagents in the Minis Transit TKO, lipofectins, lipofectamines, cellfectins, cationic polymeric reagents (e.g., polylysin), or liposomes, as well as any other means known to a person of skills in the art.

In some embodiments, the composition of the invention may further comprise one or more additional active agents for treating or preventing tumors. In some embodiments, the additional active agent for treating or preventing tumors are selected from chemotherapeutic agents and radiotherapeutic agents, such as alkylating agents, antimetabolites, antitumor antibiotics, botanical anticancer medicines, hormones and immunotherapeutics. Examples include mitosis inhibitors, transcription inhibitors and protein synthesis inhibitors, and more specifically, vinblastine, vincristine, vindesine, vinorelbine, colchicamine, colchicine, colchicamide, podophyllotoxin, etoposide, teniposide, paclitaxel or docetaxel, camptothecin, homoharringtonine, procarbazine, asparaginase, cisplatin, carboplatin, mitoxantrone, tamoxifen, cyclophosphamide, chlorambucil hydrochloride, lomustine, semustine, cetepa, busulfan, methamphetamine, chlorambucil, fluorouracil, Tegafur, efluidin, carmofur, mercaptopurine, methotrexate, cytarabine, cyclocytidine, mercaptoguanine, hexamethylmelamine, hydroxyurea, mitomycin, doxorubicin (adriamycin), epirubicin, bleomycin, pelomycin, atorvastatin, gleevec, gemcitabine, actinomycin D, cycloheximide, topotecan and/or leuprolide; especially actinomycin D, cycloheximide, doxorubicin; and analogs, derivatives, prodrugs or metabolites thereof. The present invention found that such a composition provides an effect of synergism in inducing apoptosis in tumor cells, inhibiting growth of tumor and tumor treatment. This is unexpected.

In the combination, the antibody-TNFα fusion protein may, for example, be present at an amount of at least $10^{-3}$ ng/ml, at least $10^{-2}$ ng/ml, at least $10^{-1}$ ng/ml, at least 1 ng/ml, at least 10 ng/ml, at least $10^2$ ng/ml, at least $10^3$ ng/ml, at least $10^4$ ng/ml, at least $10^5$ ng/ml, at least 20 ng/ml, at least 40 μg/ml, or a range formed from any two of the above as the lower and upper limits, such as 20 ng/ml to 40 μg/ml, less than 30 ng/ml, less than 20 ng/ml; or an amount of at least $10^{-5}$ nM, at least $10^{-4}$ nM, at least $10^{-3}$ nM, at least $10^{-2}$ nM, at least $10^{-1}$ nM, at least 1 nM, at least 10 nM, at least $10^2$ nM, or a range formed from any two of the above as the lower and upper limits.

In the combination, the content of the one or more additional agents for treating or preventing tumors can be determined according to the relevant guidelines of medication in clinic and other conventional dosages. Or, the content may be, for example, at least 1 nM, at least 10 nM, at least 15 nM, at least 20 nM, at least 100 nM, at least 1 μM, at least 2 μM, at least 3 μM, at least 4 μM, at least 5 μM, at least 10 μM, at least 20 μM, at least 30 μM, at least 40 μM, at least 50 μM, at least 100 μM, or a range formed from any two of the above as the lower and upper limits; or at least 1 μg/ml, at least 2 μg/ml, at least 3 μg/ml, at least 4 μg/ml, at least 5 μg/ml, at least 6 μg/ml, at least 7 μg/ml, at least 8 μg/ml, at least 9 μg/ml, at least 10 μg/ml, or a range formed from any two of the above as the lower and upper limits.

In context of the composition, the fusion protein and the additional active agent may be present at a ratio equivalent to the ratio between any one of the amounts specified for the fusion proteins and any one of the amounts specified for the active agent as in the above. For example, the ratio may be equivalent to: 1-100 ng/ml to 1 nM-100 µM; such as 1-100 ng/ml to 1-20 nM, 1-100 ng/ml to 15 nM, 1 ng/ml to 1-20 nM, 100 ng/ml to 1-20 nM, 1 ng/ml to 15 nM, 100 ng/ml to 15 nM; such as 1-100 ng/ml to 1-100 µM, 1-100 ng/ml to 3-50 µM, 1-100 ng/ml to 4-40 µM, 1-100 ng/ml to 10-30 µM, 1 ng/ml to 1-100 µM or 3-50 µM or 4-40 µM or 10-30 µM, 100 ng/ml to 1-100 µM or 3-50 µM or 4-40 µM or 10-30 µM, such as 1 ng/ml to 33 µM, 100 ng/ml to 33 µM, 1 ng/ml to 11 µM, 100 ng/ml to 11 µM, 1 ng/ml to 3.7 µM, 100 ng/ml to 3.7 µM; or such as $10^{-3}$-$10^5$ ng/ml to 1-10 µg/ml, $10^{-3}$-$10^5$ ng/ml to 5 µg/ml, $10^{-3}$-$10^2$ ng/ml to 5 µg/ml, $10^{-2}$-$10^2$ ng/ml to 5 µg/ml. The phrase "equivalent to" here means that the ratio is the same, while the specific amounts of the two agents are not limited to the values as listed.

Notably, the term "composition" means that the ingredients act in cooperation, and it does not necessarily mean that the ingredients are always in the same mixture or system. For example, ingredients of a composition may be physically or spatially separated from one another, may be administered to a subject at the same time point after being mixed or not mixed, or sequentially administered to a subject at different time points, as long as they act in cooperation at the site of target. For example, according to the present application, embodiments of the composition include a kit, which may comprise one or more ingredients of the composition of the invention in one or more containers.

Applications

The antibody-TNFα fusion protein, the nucleic acid construct(s), the vector, the host cell and the composition according to the present invention can be used to induce apoptosis in tumor cells, to inhibit growth of tumor, to prevent and/or treat tumors, and can also be used for manufacturing a product, such as a medicament, a pharmaceutical formulation, a kit, etc., for these purposes.

In the context of the present application, examples of tumors include those expressing tumor-specific antigens or have high expression of tumor-associated antigens, including but not limited to tumors that are responsive to TNFα treatment. Examples of tumor-specific antigens and tumor-associated antigens include but are not limited to: ErbB family members, such as EGFR, Her-2, Her-3 and Her-4. Specifically, examples of tumors include, but are not limited to: gastric cancer, breast cancer, ovarian cancer, melanoma, bowel cancer such as colon and rectal cancer, liver cancer, pancreatic cancer, kidney cancer, lung cancer, head and neck cancer, cervical cancer, skin cancer, esophageal cancer, bone cancer and leukemia.

The antibody-TNFα fusion protein, the nucleic acid construct(s), the vector, the host cell and the composition according to the present invention can also be used in combination with an additional active agent or therapy for treating or preventing tumors. The additional active agent for treating or preventing tumors is as described in the section of "composition" above. The additional therapy may be, for example, surgery, radiotherapy and chemotherapy.

As for dosage of the fusion protein of the invention, a physician knows to determine a dosage appropriate for a patient depending on known factors including, for example, species, race, age, bodyweight, disease status and administration manner. For example, the dosage may be at least 0.1 mg/kg bodyweight, at least 0.3 mg/kg bodyweight, at least 1 mg/kg bodyweight, or at least 3 mg/kg bodyweight. The fusion protein or the composition of the present invention can be administered in various ways as appropriate, including oral administration and parenteral administration, such as injection and infusion.

As can be understood by a person of skills in the art, the features and approaches in the present disclosure can be recombined without departing from the spirit and scope of the present invention. More aspects of the invention would become obvious to a person of skills in the art from the present disclosure.

EXAMPLES

The present invention will be further illustrated with reference to the following specific examples. It will be appreciated by a person of skills in the art that various modifications and change can be made without departing from the spirit and scope of the invention.

In the following examples, unless otherwise specified, methods or processes can be conducted as conventional practiced in the art, for example, as described in "Molecular Cloning: A laboratory Manual" (3rd edition, 1989, Cold Spring Harbor Laboratory Press, New York), or by following manufacturer's instruction. DNA sequencing can be conducted using known methods or purchased from a service provider.

Example 1: Construction of Expression Plasmid for Antibody-TNFα Fusion Protein

1. Construction of Expression Plasmid for Her-2 Antibody-TNFα Fusion Protein

Trastuzumab was used as an example of Her-2 antibodies. The complete cDNAs encoding the heavy chain and the light chain of Trastuzumab were synthesized by GenScrip (USA), and were cloned into vector pUC57. The cDNA of human TNFα was obtained from OpenBiosystems (USA).

It has been shown in quite some reports that in expression and preparation of monoclonal antibodies, deletion of lysine residue(s) at C-terminal of heavy chains is common. Therefore, we removed this lysine residue to ensure integrity of the antibody fusion protein.

The gene encoding the heavy chain of Trastuzumab and the gene encoding TNFα was connected by a two-step polymerase chain reaction (PCR) process. In the first step, the gene of the heavy chain was amplified using synthetic DNA primers by PCR (High-Fi Polymerase Pfx, Invitrogen):

5'-primer M13-F (SEQ ID NO: 5): 5'-TGTAAAACGACGGCCAGT-3', on vector;

3'-primer KDP004 (SEQ ID NO: 6): 5'-TCCTGGGGACAGTGACAGTG-3', specific for the antibody heavy chain gene.

The gene encoding the TNFα moiety was amplified by PCR in the same way:

```
5'-primer KDP045 (SEQ ID NO: 7):
5'-CACTGTCACTGTCCCCAGGAGTCAGATCATCTTCTCGAACC-3';

3'-primer BGH-R (SEQ ID NO: 8):
5'-AACTAGAAGGCACAGTCGAGGC-3', on vector.
```

Therein, sequence of the first 20 nucleotides in the TNF-F primer was complementary to the nucleotide sequence in the Her2-R primer, so that the two fragments from PCR could be connected in the second step of overlap extension PCR.

The two resultant PCR fragments were purified using DNA Gel Purification (Tiangen Biotech (Beijing) Co., Ltd.) before the second step of overlap PCR. The purified DNA fragments were 3-times diluted with eluent to facilitate ligation via overlap PCR:

```
5'-primer: still M13-F (SEQ ID NO: 5);

3'-primer BGH-R (SEQ ID NO: 8):
5'-TGGTGGTGTCTAGAGACTCACAGGGCAATGATCCC-3',
``` containing an XbaI restriction site for cloning.

A NotI restriction site was placed upstream to the transcription initiation site of the gene of Trastuzumab heavy chain. The fragment obtained from overlap PCR was gel purified and subjected to NotI/XbaI double digestion (Takara). The digested PCR fragment was cloned into the correspondingly digested expression vector for mammalian cells. The expression vector for mammalian cells was a modified pcDNA3.1 plasmid (Invitrogen), wherein the anti-neomycin gene was replaced by DHFR (dihydrofolate reductase) gene. The modified vector is useful for screening for mammalian cells having high expression of stably exogenous proteins. The obtained recombinant plasmid was transfected into competent bacterial strain DH5a. Positive colonies containing the correct recombinant plasmid were identified by colony PCR. The recombinant plasmid was purified, and correct sequence of the recombinant gene of Trastuzumab heavy chain-TNFα was confirmed by restriction digestion and sequencing.

The cDNA of Trastuzumab's light chain was sub-cloned into another pcDNA3.1 plasmid using enzymes NotI and XbaI.

2. Construction of Expression Plasmid for EGFR Antibody-TNFα Fusion Protein

Cetuximab was used as an example of EGFR antibodies. The gene encoding the heavy chain variable region of Cetuximab (VH, with signal peptide) and the gene encoding the light chain variable region of Cetuximab (VL, with signal peptide) were synthesized by Genewiz (Beijing) Co. Ltd., and were cloned into vector pUC57.

To construct the gene of Cetuximab heavy chain-TNFα, first, the Cetuximab VH gene and IgG1 Fc gene were connected by PCR to obtain gene of a complete heavy chain of Cetuximab; and then, the obtained gene of Cetuximab heavy chain was connected with the TNFα gene by PCR to obtain the gene of Cetuximab heavy chain-TNFα. The obtained PCR fragment was digested with NotI and XbaI, and cloned into correspondingly digested expression vector for mammalian cells. In this example, the expression vector for mammalian cells was a modified pcDNA3.1 plasmid (Invitrogen) wherein the anti-neomycin gene was replaced by the gene of rat glutamine synthetase (GS).

The primers for PCR amplification of Cetuximab VH gene were M13-R (Forward, 5'-CAGGAAACAGC-TATGACC, SEQ ID NO: 9) and KDP077 (Reverse, 5'-GCTAGGCCCCTTTGTTGATGCGGCGGACACGGT-CACGAGGG, SEQ ID NO: 10). The primers for amplifying IgG1 Fc fragment were KDP020 (5'-GCAT-CAACAAAGGGGCCTAGC, SEQ ID NO: 11) and BGH-R (5'-AACTAGAAGGCACAGTCGAGGC, SEQ ID NO: 12).

The PCR fragment of Cetuximab VH gene and the fragment of IgG1 Fc were connected by overlap extension PCR using primer KDP092 (Forward, 5'-ATG-GAACGCGGCCGCCACC, SEQ ID NO: 13) and primer KDP093 (Reverse, 5'-TCTAGCATTTAGGTGACAC, SEQ ID NO: 14). The obtained fragment of full-length heavy chain was cloned into said expression vector using restriction enzymes NotI/XbaI.

Then gene encoding Cetuximab heavy chain-TNFα was cloned according to the procedure as described for the gene encoding Trastuzumab heavy chain-TNFα. The PCR primers for amplifying the gene of Cetuximab heavy chain were primer CMV-P (Forward, 5'-CGCAAATGGGCGGTAGGCGTG, SEQ ID NO: 15) and primer KDP004 (SEQ ID NO: 6). The primers for amplifying the TNFα gene were KDP045 (SEQ ID NO: 7) and BHG-R (SEQ ID NO: 12). The two genes were connected using PCR primers KDP033 (5'-AGCTTGGTACCCTCGAGG, SEQ ID NO: 16) and KDP093 (SEQ ID NO: 14). The obtained gene of Cetuximab heavy chain-TNFα was cloned into said expression vector using restriction enzymes NotI/XbaI.

To construct gene of the Cetuximab light chain, the gene of light chain variable region (VL) and the gene of constant region (kappa) were amplified by PCR. The PCR primers for the VL gene were M13-R (SEQ ID NO: 9) and KDP094 (GACAGATGGAGCGGC-CACAGTTCGCTTCAGCTCCAGCTTTGTTCC, SEQ ID NO: 17). The PCR primers for the kappa gene were KDP010 (ACTGTGGCCGCTCCATCTGTC, SEQ ID NO: 18 and BGH-R (SEQ ID NO: 12). The PCR fragment of Cetuximab VL gene and the PCR fragment of the kappa gene were connected by overlap extension PCR using primer M13-R (SEQ ID NO: 9) and primer KDP093 (SEQ ID NO: 14). The obtained fragment of the full-length light chain gene was cloned into said expression vector using NotI/XbaI restriction enzymes.

Example 2: Establishment of Cell Line Stably Expressing Antibody-TNFα Fusion Protein The host cell CHO DG44 was obtained from Invitrogen. The cells were cultured and subcultured according to the CHO DG44 manual from Invitrogen. Non-transfected cells were suspension cultured in CD DG44 medium (Invitrogen) supplemented with 8 mM L-glutamine (Sigma) and 5 μg/ml recombinant human insulin. CHO-K cell was obtained from the Cell Bank of the Type Culture Collection Committee of Chinese Academy of Sciences (Shanghai). The primary cells exhibited adherent growth in a serum-supplemented medium, and were habituated to be capable of suspension growth in a serum-free medium (chemically defined medium, abbr. "CD"). In this example, the CHO DG44 cells were used to express the Trastuzumab-TNFα fusion protein, and the CHO-K cells were used to express the Cetuximab-TNFα fusion protein.

Briefly, the strain stably expressing the Trastuzumab-TNFα fusion protein was constructed as follows. The expression plasmid of the fusion protein's heavy chain and the expression plasmid of the fusion protein's light chain were prepared using the Plasmid Maxi Preparation Kit (TIANGEN, China). 100 μg pcDNA3.1 comprising the antibody heavy chain-TNFα and 100 μg pcDNA3.1 comprising the antibody light chain prepared according to Example 1 were linearized by digestion using restriction endonuclease EcoRI. The DG44 cells were subcultured for at least three passages before transfection. $1 \times 10^7$ DG44 cells were mixed with the digested plasmids in 0.8 ml CD DG44 growth medium and then transferred in to a 0.4-cm pulser (Bio-Rad), wherein the cell/plasmid mixture was pulsed on Gene Pulser Xcell (Bio-Rad). The transfected cells were then cultured in a T-75 square flask containing 20 ml growth medium for 24 hours at 37° C. in 8% $CO_2$ in incubator.

After the 24-hour incubation, the transfected cells were plated on a 96-well plate by limiting dilution, using the OptiCHO medium as the medium for screen, wherein the medium was supplemented with 8 mM glutamine, 5 µg/ml recombinant human insulin and 100 nM methotrexate (MTX, Sigma). The cells were incubated at 37° C. in 8% $CO_2$ in incubator. 3 weeks later, culture liquid from the wells observed with colony formation was examined by ELISA using alkaline phosphatase-conjugated goat anti-human IgG Fc antibody (Jackson ImmunoResearch Lab), whereby clones with the highest expression were picked and amplified, then assayed via ELISA and amplified again, which finally ended up with 12 cell lines with highest stable expression.

The 12 clones were cultured under stress using an increasing gradient of MTX concentrations for enhanced expression. Totally three rounds of incubation under stress (500 nM, 2 µM and 10 µM of MTX) were conducted, each for about 3 weeks. After the 3-rounds stress incubation, the 12 clones were tested for antibody expression, whereby 4-5 cell lines with increased antibody expression were obtained.

Without experiencing the MTX stress, the cell lines with stable antibody expression were low in expression level. After 3 rounds of stress treatment, with the MTX magnitude increasing from 0.1 µM to 10 µM in the culture medium, the antibody expression was significantly increased in most of the cell lines exposed to the stress. From these cell lines, one strain (#1G5) was pick and plated on a 96-well plate and cultured by limiting dilution to obtain a monoclonal strain with high expression of the antibody fusion protein. Cell strains stably expressing Cetuximab-TNFα fusion protein was constructed by the method and steps outlined as follows. CHO-K cells were co-transfected with plasmid encoding the chain of Cetuximab heavy chain-TNFα and plasmid encoding Cetuximab light chain via pulse-transfection. The transfected cells were plated on a 96-well plate and cultured by limiting dilution in medium containing L-aminosulfoxide methionine (MSX) to screen for strains stably transfected with the plasmids. Cell lines with positive antibody expression were picked by ELISA. Specifically, supernatant comprising said cells were added onto a ELISA plate coated with recombinant human EGFR protein; antibody was detected using alkaline phosphatase (AP) conjugated goat anti-human IgG1 Fc antibody; cell lines having high expression were picked and amplified, then subjected to the next round of screening; and thereby, CHO-K cell lines with stable and high expression of Cetuximab-TNFα fusion protein were obtained.

Example 3: Preparation, Purification and Identification of Antibody-TNFα Fusion Protein The cell line with high expression of antibody-TNFα obtained according to Example 2 was cultured and amplified to 2 liters. Supernatant of the culture was harvested for purification and preparation of the antibody. The purification was Protein-A affinity chromatography (POROS MabCapture A, Life Tech) followed by anion exchange chromatography (flow through).

The purified antibody was analyzed by reducing and non-reducing SDS-PAGEs and HPLC-SEC (High Pressure Liquid—Molecular Sieve, TSKgel G3000SWXL, TOSOH Bioscience).

Results and Analysis

As shown by the gel of non-reducing SDS-PAGE in FIG. 2A, the intact Trastuzumab-TNFα fusion protein exhibited a molecular weight slightly below 200 kDa, which was very close to the theoretical value of 180 kDa. As shown by the gel of reducing SDS-PAGE in FIG. 2B, the chain of Trastuzumab heavy chain-TNFα in the fusion protein exhibited a molecular weight at 70 kDa, which was also consistent with the theoretical molecular weight (73 kDa).

The HPLC-SEC result of the Trastuzumab-TNFα fusion protein was shown in FIG. 2C. Therein, a peak of the fusion protein was detected at near 600 kDa, which was not consistent with the molecular weight shown by SDS-PAGE. This can be assumedly explained in two ways. First, the Trastuzumab-TNFα fusion protein molecules formed a trimer. Free TNFα molecule is trimeric in vivo, and the monomeric Trastuzumab-TNFα fusion protein in the described example comprised two TNFα molecules; then, Trastuzumab-TNFα fusion protein molecules need to aggregate into a trimer to allow formation of the TNFα trimer. Secondly, the Trastuzumab-TNFα fusion protein had a fairly loose structure, which exhibited the appearance of a large molecular weight in HPLC-SEC.

Figure 3B:
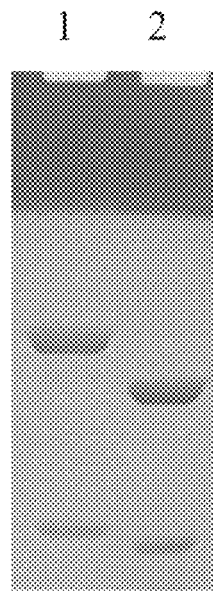
Figure 3C:
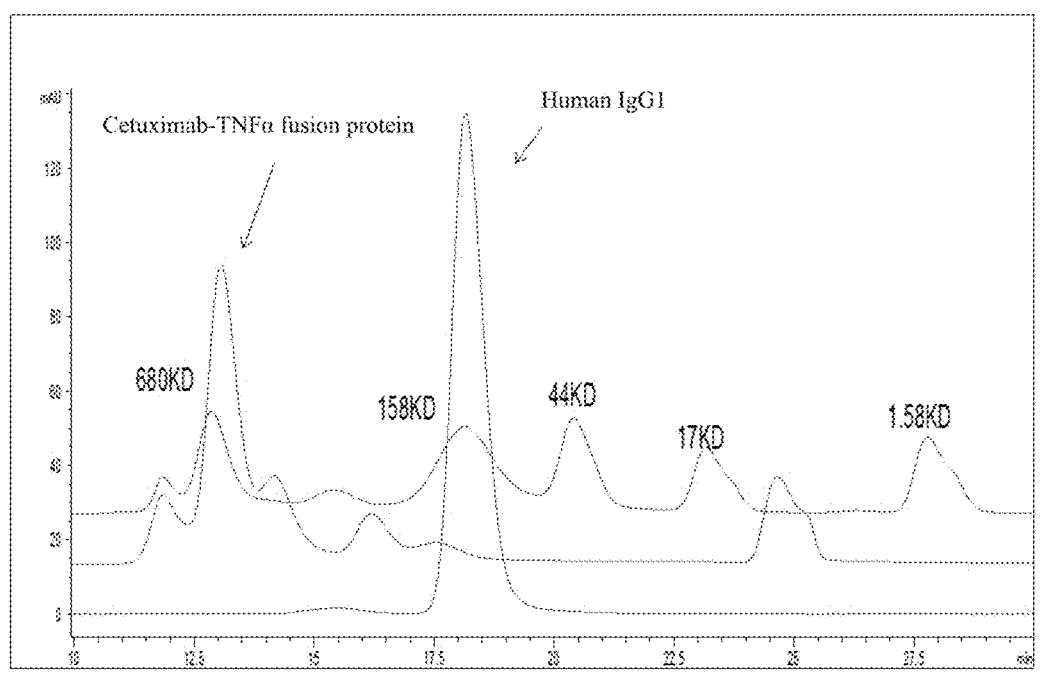

Non-reducing SDS-PAGE, reducing SDS-PAGE and HPLC-SEC results of the Cetuximab-TNFα fusion protein were the same, as shown in FIGS. 3A-3C. As shown by the gel of non-reducing SDS-PAGE, the intact Cetuximab-TNFα fusion protein exhibited a molecular weight slightly higher than native human IgG1, which was very close to the theoretical value of 180 kDa (FIG. 3A). As shown by the gel of reducing SDS-PAGE in FIG. 3B, the chain of Cetuximab heavy chain-TNFα in the fusion protein exhibited a molecular weight higher than that of the heavy chain of native human IgG1, which is also consistent with the theoretical molecular weight (73 kDa). The HPLC-SEC peak of the Cetuximab-TNFα fusion protein was also detected at 600 kDa (FIG. 3C), indicating a structure likely consistent the Trastuzumab-TNFα fusion protein.

Example 4: Tumor Antigen Binding of Antibody-TNFα Fusion Protein

Binding of the prepared Trastuzumab-TNFα fusion protein to extracellular domain (ECD) of the membrane protein Her-2 was studied via ELISA, in comparison with the antibody Trastuzumab (CTTQ Pharmaceutical Group Co., Ltd).

25 nM recombinant human Her-2 ECD (donated by ANKEBIO (Group) Co., Ltd.) was dissolved in 50 mM $NaHCO_3$ (pH 9.6). The recombinant protein (50 µL) was added into wells of a 96-well ELISA plate and was stored at 4° C. overnight in refrigerator. The next day, the ELISA plate was washed 3 times with PBST (PBS with 0.05% Tween-20), and then blocked with 100 µl/well blocking buffer being PBST comprising 3% BSA. The ELISA plate was incubated at 37° C. for 1 hour in incubator. The Trastuzumab-TNFα fusion protein and the Trastuzumab antibody were each prepared into 3-fold serial dilutions in binding buffer being PBST with 1% BSA. The blocking buffer was drained, and the fusion protein and Trastuzumab in the 3-fold serial dilutions were added (50 µL/well) to react at 37° C. for 1 hour in incubator. The dilutions were removed, the ELISA plates were washed 3 times with PBST, and the secondary antibody (alkaline phosphatase-conjugated goat anti-human IgG Fc antibody, Jackson ImmunoResearch Lab) was added (50 µL/well) to react at 37° C. for 1 hour in incubator. The staining antibody was removed, PBST wash buffer was added (200 μL/well) and the ELISA plates were placed on an orbital shaker at 100 rpm for 5 minutes; then, the wash buffer was removed and the washing steps were repeated 4 times. The developer solution (PNPP) was added (50 μl/well) and the ELISA plates were incubated at 37° C. in incubator for development. The plates were read on a microplate reader at 405 nm/655 nm.

Binding of the prepared Trastuzumab-TNFα fusion protein to the Her-2 surface protein was also assayed via flow cytometry. Three Her-2 positive human tumor cell lines, i.e., human pancreatic cancer cell line PANC-1, human ovarian cancer cell line SKOV-3 and human breast cancer cell line SKBR-3 (all from Cell Bank of the Chinese Academy of Sciences) were used. The cells were prepared in pre-cooled FACS working buffer (PBS with 0.1% FBS) at $3\times10^6$ cells/ml and divided into aliquots of 100 μl/tube, which were blocked on ice for 1 hour. The Trastuzumab-TNFα fusion protein and Trastuzumab were each diluted to 10 μg/ml in the FACS working buffer. The dilutions (10 μL) were added into cell suspension (100 μL) and incubated on ice for 30 minutes. At the end of incubation, to each tube, FACS working buffer (1 ml) was added and mixed with the cell suspension by vortex; the cell suspension was then centrifuged at 1200 rpm for 5 minutes; the supernatant was discarded and the washing steps were repeated once. FITC-labeled goat anti-human IgG Fc antibody (Jackson ImmunoResearch Lab) was diluted in the FACS working buffer, and then added into the cell suspension (10 μL per tube) at a final concentration of 1 μg/ml. The tubes were incubated on ice for 30 minutes in dark. At the end of incubation, to each tube, FACS working buffer (1 ml) was added and mixed with the cell suspension by vortex; the cell suspension was then centrifuged at 1200 rpm for 5 minutes; the supernatant was discarded and the washing steps were repeated once. The cells were assayed on flow cytometer C6 (BD Biosciences).

Results and Analysis

Figure 4A:
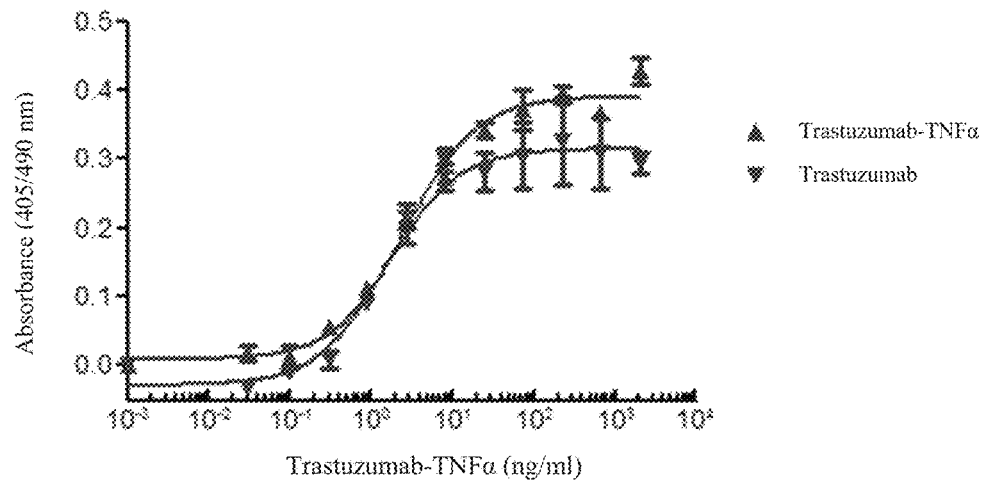
FIGS. 4A-4B: Her-2 antibody-TNFα fusion protein binding to Her-2 molecule in vitro.

As shown by the ELISA result in FIG. 4A, the Trastuzumab-TNFα fusion protein was capable of specifically binding to the Her-2 ECD, with a $EC_{50}$ of 0.018 nM, which was comparable to the binding capacity ($EC_{50}$ of 0.008 nM) of Trastuzumab binding.

Figure 4B:
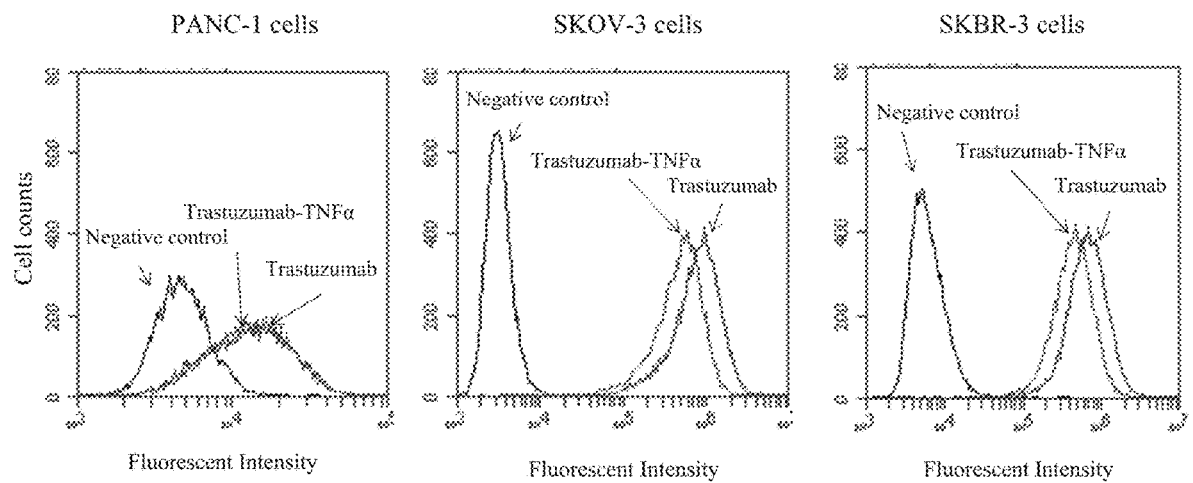

As shown by the flow cytometry results in FIG. 4B, the Trastuzumab-TNFα fusion protein was capable of binding to all the three Her-2 positive cell lines in test, exhibiting a binding capacity comparable to the antibody Trastuzumab. As seen, the fusion protein of the invention preserved the intact binding property of the antibody.

Example 5: Binding of Antibody-TNFα Fusion Protein to TNFR In Vitro

Binding of the Trastuzumab-TNFα fusion protein to the extracellular domain of human TNFR2 (sTNFR) was studied via ELISA. The fusion protein of sTNFR2 and IgG Fc (Celgen Biopharmaceutical Co., Ltd.) was diluted to 1 nM in 50 mM NaHCO$_3$ (pH 9.6). The solution (50 μL) was added into the wells of a 96-well ELISA plate and was stored at 4° C. overnight in refrigerator. The next day, the ELISA plate was washed 3 times with PBST (PBS with 0.05% Tween-20), and then blocked with 100 μl/well blocking buffer being PBST comprising 3% BSA. The ELISA plate was incubated at 37° C. for 1 hour in incubator. The Trastuzumab-TNFα fusion protein obtained according to Example 3 was prepared into 4-fold serial dilutions in binding buffer being PBST+1% BSA. The blocking buffer was drained, and the fusion protein in the 4-fold serial dilutions was added (50 μL/well) to react at 37° C. for 1 hour in incubator. The dilutions of fusion protein were removed, the ELISA plates were washed 3 times with PBST, and the secondary antibody (alkaline phosphatase-conjugated goat anti-human IgG Fab antibody, Jackson ImmunoResearch Lab) was added (50 μL/well) to react at 37° C. for 1 hour in incubator. The staining antibody was removed, PBST wash buffer was added (200 μL/well) and the ELISA plates were placed on an orbital shaker at 100 rpm for 5 minutes; then the wash buffer was removed and the washing steps were repeated 4 times. The developer solution (PNPP) was added (50 μl/well) and the ELISA plates were incubated at 37° C. in incubator for development. The plates were read on a microplate reader at 405 nm.

Results and Analysis

Figure 5:
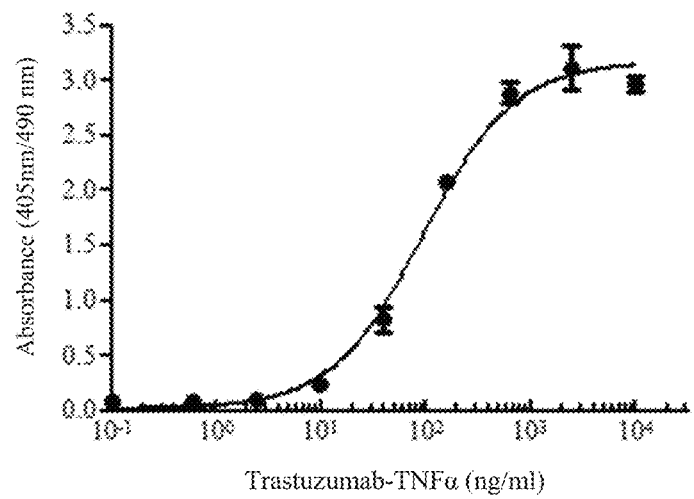
FIG. 5: ELISA of the Her-2 antibody-TNFα fusion protein's binding to TNFR type II (also known as "TNFR2") in vitro. A 96-well ELISA plate was coated with the Fc fusion protein of recombinant human TNFR2 ECD, and the antibody bound to TNFR2 ECD was detected using alkaline phosphatase-labeled goat anti-human IgG1 Fab antibody.

As shown in FIG. 5, the Trastuzumab-TNFα fusion protein bound to sTNFR2-Fc with an $EC_{50}$ of 0.5 nM, which suggests that the Her-2 antibody-TNFα fusion protein of the invention specifically binds to TNFR with high affinity.

Example 6: Apoptosis in L929 Cells Induced by Antibody-TNFα Fusion Protein

The Trastuzumab-TNFα fusion protein and the Cetuximab-TNFα fusion protein were tested on cytotoxicity in mouse fibroblasts L929, in comparison with recombinant human TNFα protein.

L929 cells (Cell Bank of the Chinese Academy of Sciences (Shanghai)) were cultured in RPMI1640 medium with 10% FBS (Invitrogen). The day before experiment, the L929 cells (10000 cells/well) were added onto a 96-well plate and incubated at 37° C. in a 5% CO$_2$ in incubator. The next day, the antibody-TNFα fusion protein and the recombinant human TNFα in 3-fold serial dilutions in the cell growth medium were added into the cells to final concentrations from 0 to 1.18 nM (totally ten concentrations). After incubation for another 20 hours, the cells were stained with crystal violet, and the plates were read on a microplate reader at 570 nm.

Results and Analysis

Figure 6A:
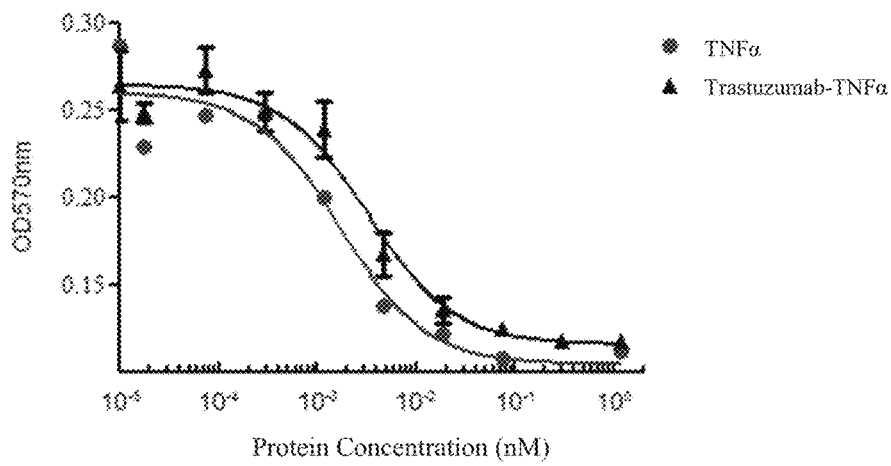
FIGS. 6A-6B: Apoptosis in L929 cells induced by the Her-2 antibody-TNFα fusion protein and by the EGFR antibody-TNFα fusion protein.
Figure 6B:
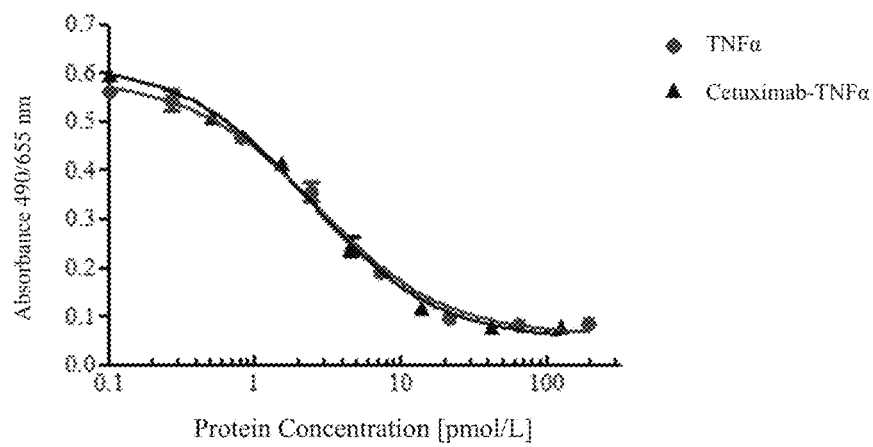

As shown in FIGS. 6A and 6B, the recombinant human TNFα induced apoptosis in L929 cells with an IC50 of 0.4-1.7 pM, and the Trastuzumab-TNFα fusion protein induced apoptosis in L929 cells with an IC50 of 3.2 pM (FIG. 6A). The Cetuximab-TNFα fusion protein induced apoptosis in L929 cells with an IC50 of 0.6 pM (FIG. 6B). These suggest that the antibody-TNFα fusion proteins of the invention highly preserved the activity of TNFα to induce apoptosis.

Example 7: Cytotoxicity of Her-2 Antibody-TNFα Fusion Protein on Her-2 Positive Human Gastric Cancer Cells Human gastric cancer cell NCI-N87 with high expression of Her-2 protein is less sensitive to Trastuzumab. Trastuzumab induces moderate apoptosis in NCI-N87 cells only at fairly high concentrations. To study activity of the Her-2 antibody-TNFα fusion protein of the invention in inducing apoptosis in NCI-N87 cells, (1) the Trastuzumab-TNFα fusion protein, (2) a (Trastuzumab+TNFα) mixture and (3) TNFα were compared for their impacts on viability in NCI-N87 cells.

The Her-2 positive human gastric cancer cells NCI-N87 (Cell Bank of the Chinese Academy of Sciences (Shanghai)) were cultured and subcultured in RPMI medium 1640 supplemented with 10% FBS (Gibco). The day before experiment, the cells (1×10⁶ cells/well) in growth medium (150 μl) were added onto a 96-well plate. The next day, the Trastuzumab-TNFα fusion protein, TNFα and the Trastuzumab+TNFα mixture (PeproTech, USA) (a mixture with the total amount of proteins substantially equivalent to that of the antibody-TNFα fusion protein by weight, with the antibody to TNFα (dimeric) ratio by weight being 5:1, approximately 2 molecules of monomeric TNFα per antibody molecule) prepared in serial dilutions in the growth medium were added (50 μl/well) into the cells on the 96-well plate, mixed and cultured for another 60 hours in incubator. Cell viability was detected using MTT assay and cell viability using CCK-8.

Results and Analysis

First, we examined and compared the effects in killing NCI-N87 between the Trastuzumab-TNFα fusion protein and the Trastuzumab antibody. Three stages of effects were observed with the Trastuzumab-TNFα fusion protein in NCI-N87 cells: at concentrations below 30 ng/ml, the fusion protein effectively induced apoptosis in cells; at concentrations between 20 ng/ml and 40 μg/ml, the killing decreased with increase in concentration; and at concentrations above 40 μg/ml, the killing increased with increase in concentration (data not shown). Trastuzumab did not substantially impact survival of NCI-N87 cells at all concentrations in test (data not shown).

Figure 7A:
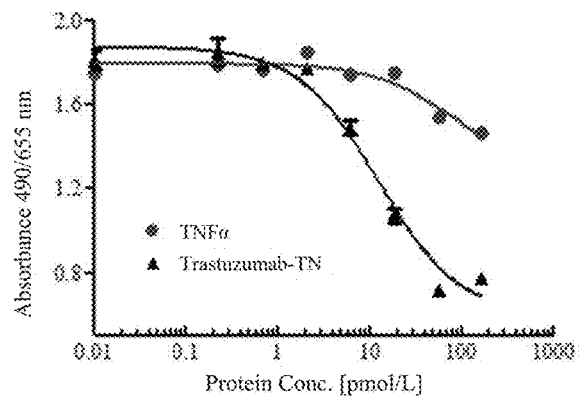
FIGS. 7A-7C: Apoptosis in Her-2 positive human gastric cancer cells NCI-N87 induced by the Her-2 antibody-TNFα fusion protein.

Next, we studied killing in NCI-N87 cells by the fusion protein at low concentrations, in comparison with TNFα. As shown in FIG. 7A, at concentrations below 20 ng/ml, the fusion protein exhibited increasing capability of inducing apoptosis with increase in concentration, with an $IC_{50}$ of 1-2 ng/ml. In comparison, TNFα induced no or little apoptosis in NCI-N87 cells at corresponding concentrations.

Figure 7B:
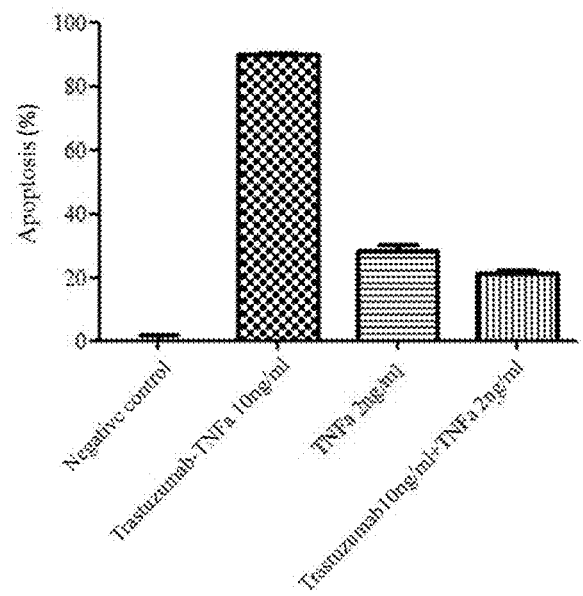
Figure 7C:
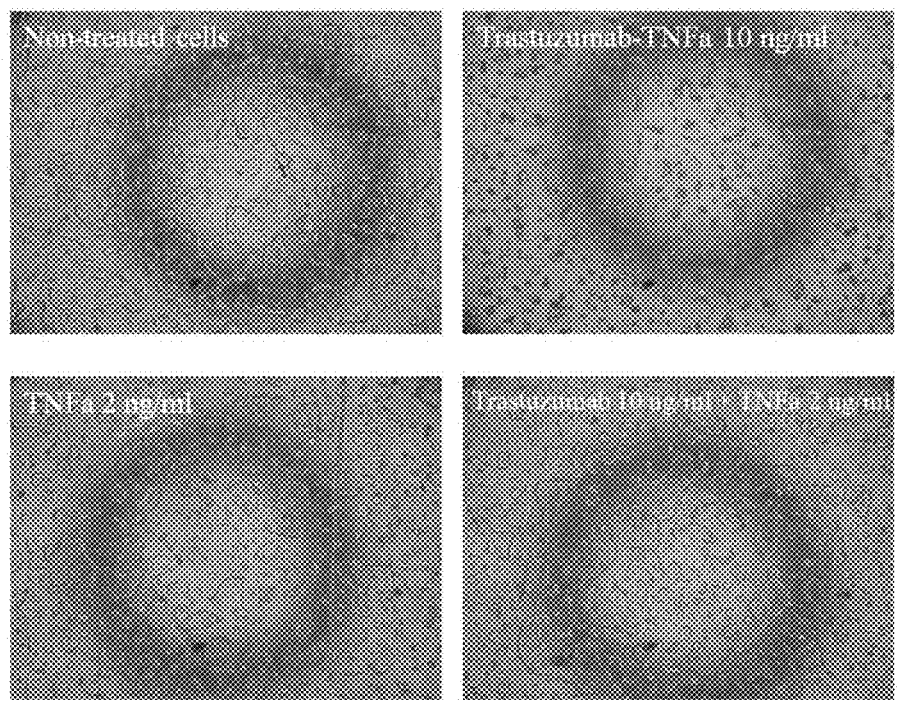

Then, we studied the effect of the TNFα+Trastuzumab mixture on survival in NCI-N87 cells. NCI-N87 cells were treated with a mixture prepared by mixing 2 ng/ml TNFα and 10 ng/ml Trastuzumab, which corresponded to 10 ng/ml of Trastuzumab-TNFα fusion protein. Apoptosis was detected, in comparison with 10 ng/ml of the Her-2 antibody-TNFα fusion protein and with 2 ng/ml of TNFα. As shown in FIG. 7B, 10 ng/ml of the antibody-TNFα fusion protein induced an apoptosis of 90%, while the TNFα+Trastuzumab mixture an apoptosis of less than 30%. Morphology of the treated cells under microscopy was shown in FIG. 7C.

There results suggest that the Her-2 antibody-TNFα fusion protein of the invention has a unique profile of effects on cell survival, and exhibits an effect of synergism as compared with TNFα alone, and a simple blend of the Her-2 antibody and TNFα.

Example 8: Cytotoxicity of EGFR Antibody-TNFα Fusion Protein on EGFR Positive Human Gastric Cancer Cells Human gastric cancer cell NCI-N87 expresses EGFR protein. To study activity of the EGFR antibody-TNFα fusion protein of the invention in inducing apoptosis in NCI-N87 cells, (1) the Cetuximab-TNFα fusion protein and (2) a mixture of Cetuximab mAb+TNFα were compared for impacts on viability in NCI-N87 cells.

EGFR-positive human gastric cancer cells NCI-N87 (Cell Bank of the Chinese Academy of Sciences (Shanghai)) were cultured and subcultured in RPMI medium 1640 supplemented with 10% FBS (Gibco). The day before experiment, the cells (1×10⁶ cells/well) in growth medium (150 μl) were added onto a 96-well plate. The next day, the Cetuximab-TNFα fusion protein and the Cetuximab+TNFα mixture (PeproTech, USA) prepared in serial dilutions in the growth medium were added (50 μl/well) into the cells on the 96-well plate, mixed and cultured for another 48 hours in incubator. Cell viability was assayed using CCK-8.

Results and Analysis

Figure 8:
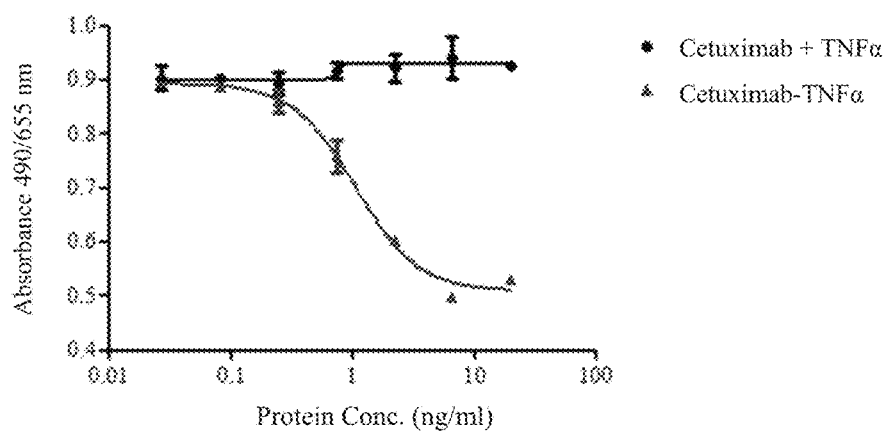
FIG. 8: Apoptosis in EGFR-positive human gastric cancer NCI-N87 cells induced by the EGFR antibody-TNFα fusion protein.

As shown in FIG. 8, the Cetuximab-TNFα fusion protein induced apoptosis in NCI-N87 cells with an IC50 of about 5.7 pM, while no apoptosis was detected with the Cetuximab+TNFα mixture even at 110 pM.

Example 9: Synergistic Induction of Apoptosis by Her-2 Antibody-TNFα Fusion Protein Combined with Anti-Tumor Chemotherapeutic in Her-2 Positive Human Tumor Cells In the following, the Her-2 positive tumor cells were all obtained from the Cell Bank of the Chinese Academy of Sciences. BT474 cell and NCI-N87 cells were cultured in RPMI 1640 medium, SKBR-3 in DMEM (Invitrogen) and SKOV-3 in McCOY's 5A medium (Invitrogen), all these media contained 10% FBS. The cells were incubated in the media added with different chemotherapeutics at different concentrations for 2 days: actinomycin D (MedChem Express) and doxorubicin (MedChem Express); then, the Trastuzumab-TNFα fusion protein was added at different concentrations and the cells were incubated for another 20 hours. Cell viability was detected by MTT assay.

Results and Analysis

Figure 9A:
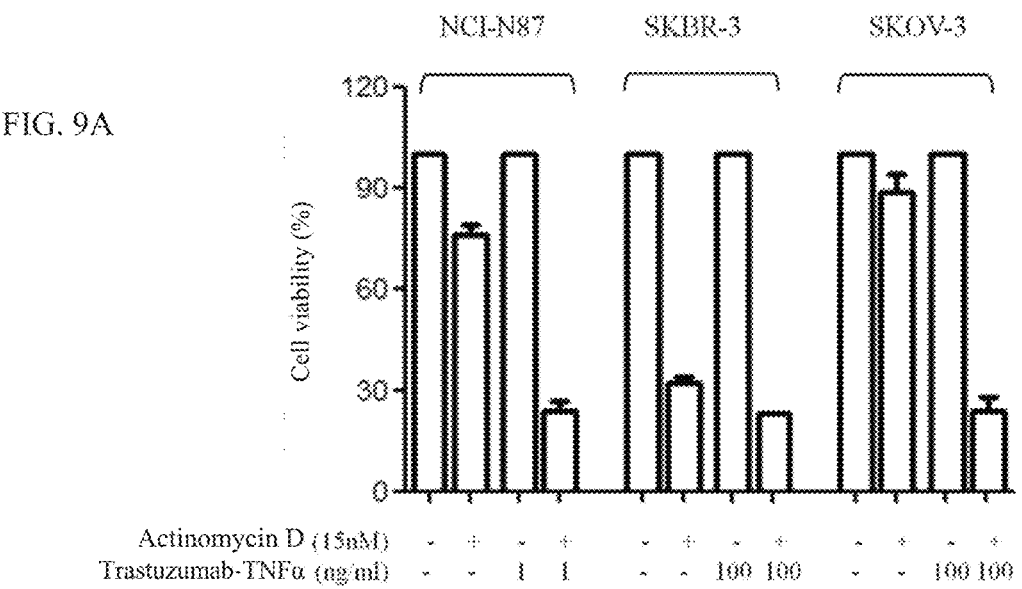
FIGS. 9A-9B: Apoptosis in Her-2 positive human tumor cells induced synergistically by the Her-2 antibody-TNFα fusion protein and a tumor toxic chemotherapeutic agent.
Figure 9B:
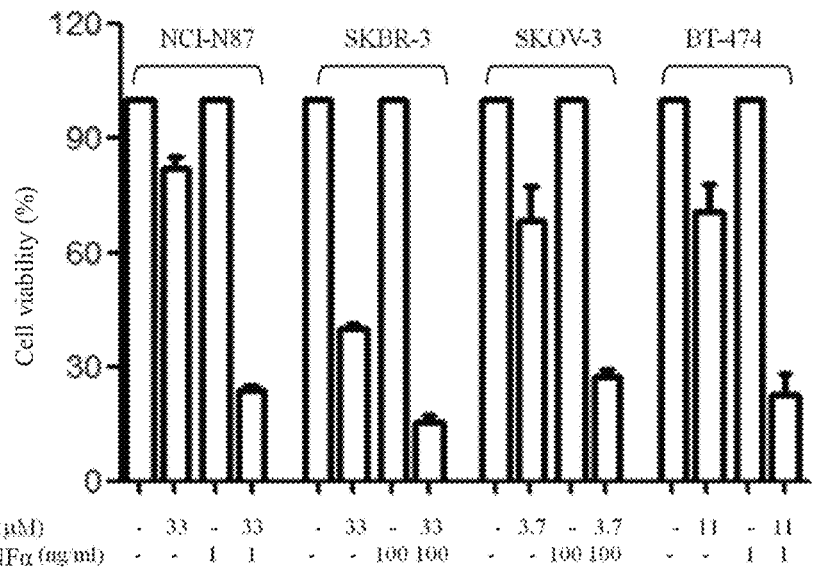

As shown, an effect of synergism was observed with both the combination of Trastuzumab-TNFα fusion plus actinomycin D (FIG. 9A) and the combination of the fusion protein plus doxorubicin (FIG. 9B).

As shown in FIG. 9A, the Trastuzumab-TNFα fusion protein in combination with actinomycin D exhibited a very strong effect of synergism in inducing apoptosis in SKOV-3 cells. Neither 100 ng/ml of Trastuzumab-TNFα fusion protein nor 15 nM of actinomycin D, when used alone, had an impact on survival of SKOV-3 cells, while the two in combination induced an apoptosis of 80%. Similarly, in NCI-N87 cells, no apoptosis was observed with 1 ng/ml of the antibody-TNFα fusion protein and 15 nM actinomycin D induced an apoptosis of 25%, while the two in combination induced an apoptosis of 80%. These indicate a significant effect of synergism. A relatively weak effect of synergism was observed with the Trastuzumab-TNFα fusion protein in combination with actinomycin D in SKBR-3 cells, where 15 nM actinomycin D alone was capable of inducing a 70% apoptosis.

The Trastuzumab-TNFα fusion protein in combination with doxorubicin exhibited a fairly strong effect of synergism in inducing apoptosis in NCI-N87 and BT-474 cells. 1 ng/ml of Trastuzumab-TNFα fusion protein in combination with 33 μM or 11 μM doxorubicin induced apoptosis in 80% NCI-N87 and BT-474 cells, while they had little effect on viability in these cells at said concentrations when being used alone (FIG. 9 B). The same effect of synergism in inducing apoptosis was observed with the Trastuzumab-TNFα fusion protein in combination with doxorubicin in SKBR-3 and SKOV-3 cells (FIG. 9B).

Example 10: Construction of Mouse Tumor Cells Stably Expressing Human EGFR or Human Her-2

Mouse melanoma cells B16, mouse colon cancer cells CT26 and mouse forestomach carcinoma (MFC) cells were all obtained from the cell bank of the Type Culture Collection Committee of the Chinese Academy of Sciences. The cells were cultured in RPMI1640/10% FBS medium (Gibco).

The gene for human Her-2 expression was cloned in the expression vector pcDNA3.1 (Invitrogen); the recombinant plasmid was transfected into the three mouse tumor cells using Lipofectamine 3000 (Invitrogen); the transfected cells were cultured in RPMI/10% FBS medium supplemented with G418 (Sigma); and, stably transfected cells were obtained thereby. The stably transfected cells were sorted using a flow cytometer (Influx, BD Biosciences), whereby the monoclonal stable B16/Her-2, CT26/Her-2 and MFC/Her-2 cell lines with high Her-2 expression were picked.

The gene for human EGFR expression was cloned in the expression vector pCMV3 (Sino Biological Inc); the recombinant plasmid was transfected into the B16 mouse tumor cells and MFC mouse tumor cells using Lipofectamine 3000 (Invitrogen); the transfected cells were cultured in RPMI/10% FBS medium supplemented with Hygromycin B (Sigma); and, stably transfected cells were obtained thereby. The stably transfected cells were sorted using a flow cytometer (Influx, BD Biosciences), whereby the monoclonal stable B16/EGFR and MFC/EGFR cell lines with high EGFR expression were picked.

Example 11: Transcription Inhibitor and Protein Synthesis Inhibitor Enhancing Toxicity of Her-2 Antibody-TNFα Fusion Protein in Mouse Forestomach Carcinoma Cells Expressing Human Her-2 (MFC/Her-2)

Toxicity of the Her-2 antibody-TNFα fusion protein on the MFC/Her-2 cells in the presence of actinomycin D (ActD, a transcription inhibitor) or cycloheximide (CHX, a protein synthesis inhibitor) was assayed, in comparison with the toxicity in absence of ActD and CHX. The MFC/Her-2 cells were plated on a 96-well plate and cultured for 1 day, then the medium was drained and to different wells were added different concentrations of the Trastuzumab-TNFα fusion protein in combination with ActD (5 μg/ml) or CHX (μg/ml) at identical concentrations. The cells were incubated for another 20 hours. The toxicity of the antibody-TNFα proteins on cells was detected by counting living cells using the Cell Counting Kit (CCK-8). The controls were the Trastuzumab+TNFα protein mixture, wherein the total amount of proteins was substantially equivalent to that in the Her-2 antibody-TNFα fusion protein, with the antibody to TNFα (dimeric) ratio by weight being 5:1, approximately 2 molecules of monomeric TNFα per antibody molecule as in the Her-2 antibody-TNFα fusion protein molecule.

Figure 10A:
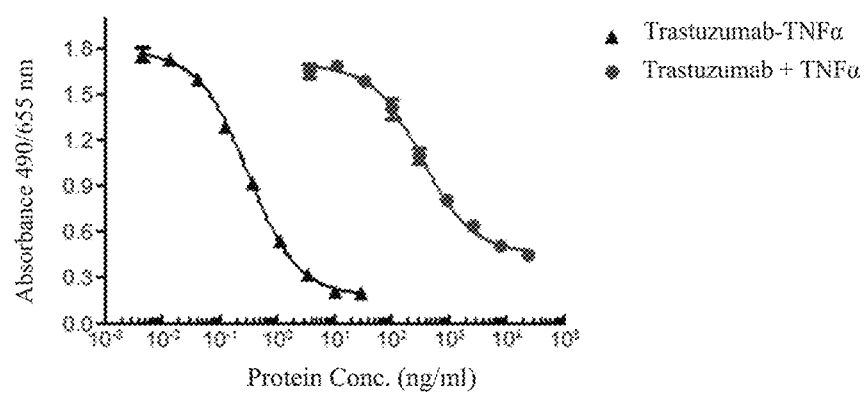
FIGS. 10A-10D: Actinomycin D (abbr. "ActD"), a transcription inhibitor, and cycloheximide (abbr. "CHX"), a protein synthesis inhibitor, enhanced toxicity of the Her-2 antibody-TNFα fusion protein in mouse forestomach carcinoma cells expressing human Her-2.

The described experiment was repeated using wild-type (wt) MFC cells, and the result was compared with that of the MFC cells expressing human Her-2.
Results and Analysis As shown in FIG. 10A, in the presence of protein synthesis inhibitor CHX (5 μg/ml), the Trastuzumab-TNFα fusion protein was highly toxic to the MFC/Her-2 cells, with a $IC_{50}$ of 0.3 ng/ml ($1.7 \times 10^{-12}$M); under the same condition, the TNFα+Trastuzumab mixture was also cytotoxic, with an $IC_{50}$ of 341 ng/ml ($1.9 \times 10^{-9}$M), i.e., with a cytotoxic concentration 1000 times of that of the antibody-TNFα fusion protein. In absence of CHX, no cytotoxicity in MFC/Her-2 was observed either with the fusion protein or the mixture (data not shown).

Figure 10B:
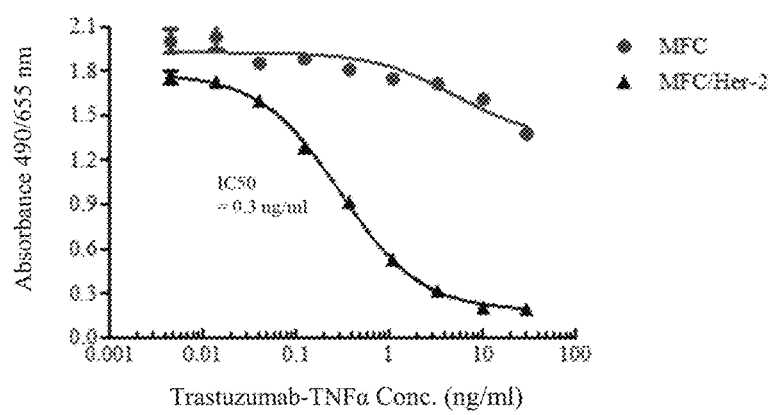

As shown in FIG. 10B, in the presence of CHX (5 μg/ml), the Trastuzumab-TNFα fusion protein induced slight cytotoxicity in wild-type MFC cells only at high concentrations. This suggests that Her-2 is the high sensitive molecule that mediates apoptosis by the Her-2 antibody-TNFα fusion protein.

Figure 10C:
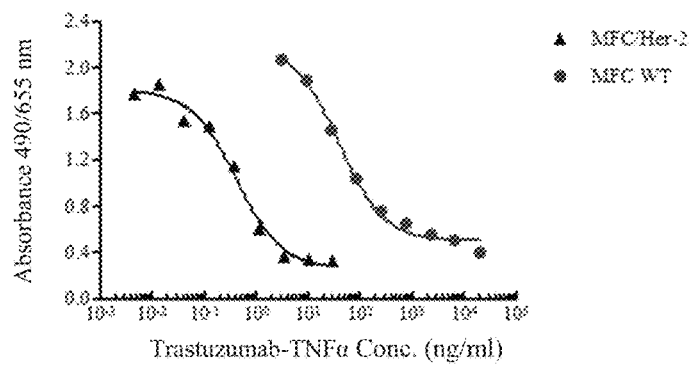
Figure 10D:
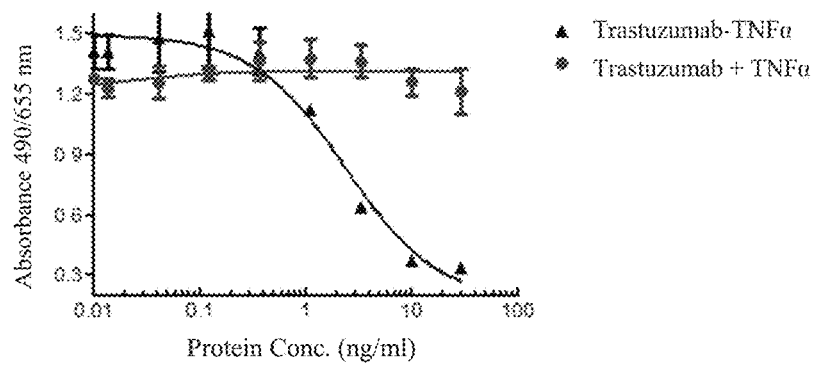

As shown in FIG. 10C, in the presence of the DNA transcription inhibitor ActD, the Trastuzumab-TNFα fusion protein induced apoptosis in MFC/Her-2 cells with an $IC_{50}$ of 0.41 ng/ml, which was far lower than the $EC_{50}$ (38 ng/ml) of apoptosis induced in the wild-type MFC cells. This also suggests that the Her-2 molecule contributes to the sensitivity to apoptosis induced by the Her-2 antibody-TNFα fusion protein. Further, as shown in FIG. 10D, in the presence of ActD, no effect on viability of MFC/Her-2 was observed with the Trastuzumab+TNFα mixture at concentrations less than 30 ng/ml.

Example 12: EGFR Antibody-TNFα Fusion Protein in Combination with Transcription Inhibitor Inducing Synergistic Effect of Apoptosis in Mouse Forestomach Carcinoma Cells Expressing Human EGFR (MFC/EGFR)

Figure 11:
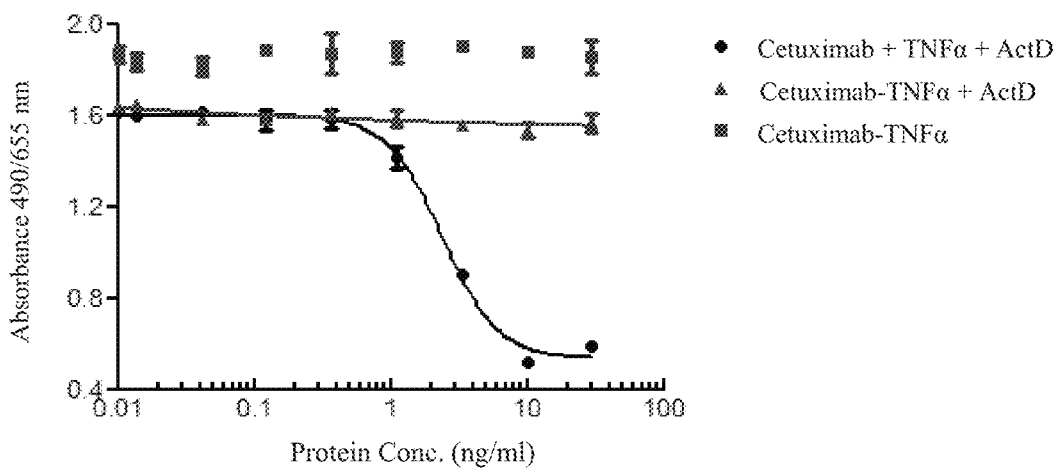
FIG. 11: A study of apoptosis in mouse forestomach carcinoma (MFC)/EGFR cells, which shows that actinomycin D (abbr. "ActD"), a transcription inhibitor, enhances toxicity of the EGFR antibody-TNFα fusion protein in mouse forestomach carcinoma cells expressing human EGFR.

The EGFR antibody-TNFα fusion proteins and the monoclonal antibody+TNFα mixture were compared on cytotoxicity in the MFC/EGFR cells in the presence of transcription inhibitor ActD at 5 μg/ml. In the Cetuximab+TNFα mixture, the ratio between the two molecules was as specified in Example 7. At the same time, cytotoxicity of the Cetuximab-TNFα fusion protein in absence of ActD was examined. The cells were incubated with said antibodies for 20 hours, and then cell viability was detected using Cell Counting Kit CCK-8.
Results and Analysis As shown in FIG. 11, in the presence of ActD, the Cetuximab-TNFα fusion protein induced apoptosis in the MFC/EGFR cells ($IC_{50}$=2.4 ng/ml), while the Cetuximab+TNFα mixture was not observed active in inducing apoptosis even at a concentration as high as 30 ng/ml. ActD synergistically enhanced the apoptosis-inducing activity of the Cetuximab-TNFα fusion protein. In absence of ActD, no apoptosis-inducing activity was observed with the Cetuximab-TNFα fusion protein at concentrations below 30 ng/ml.

Figure 12:
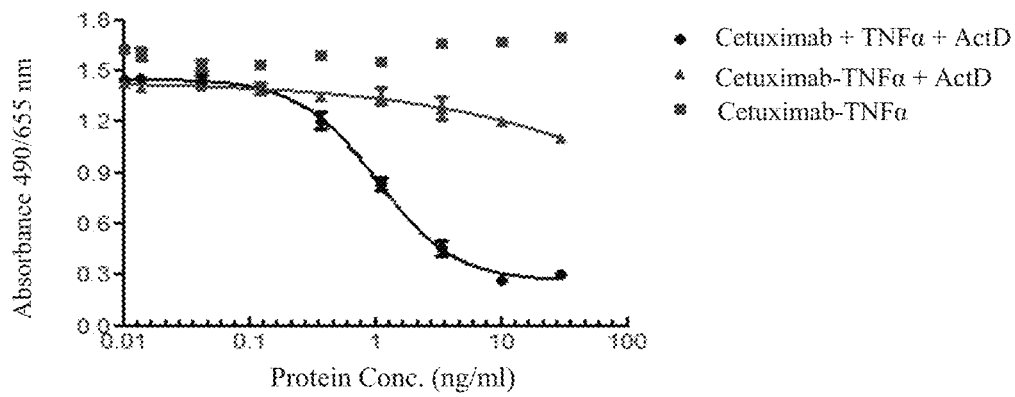
FIG. 12: A study of apoptosis mouse melanoma B16/EGFR cells, which shows that actinomycin D (abbr. "ActD"), a transcription inhibitor, enhances toxicity of the EGFR antibody-TNFα fusion protein in mouse melanoma cells B16 expressing human EGFR.

Example 13: EGFR Antibody-TNFα Fusion Protein in Combination with Transcription Inhibitor Synergistically Inducing Apoptosis in Mouse Melanoma Cells Expressing Human EGFR The EGFR antibody-TNFα fusion protein and the Cetuximab+TNFα mixture were compared on cytotoxicity in B16/EGFR cells in the presence of transcription inhibitor ActD at 5 μg/ml. The formulation of the Cetuximab+TNFα mixture was as specified in Example 7. Also examined is cytotoxicity of the EGFR antibody-TNFα fusion protein in absence of ActD. The cells were incubated with said antibodies for 20 hours, and then cell viability was detected using Cell Counting Kit CCK-8.
Results and Analysis As shown in FIG. 12, in the presence of ActD, the Cetuximab-TNFα fusion protein induced apoptosis in B16/EGFR cells ($IC_{50}$=1.0 ng/ml), while the Cetuximab+TNFα mixture was not observed active in inducing apoptosis even at a concentration as high as 30 ng/ml. ActD synergistically enhanced the apoptosis-inducing activity of the Cetuximab-TNFα fusion protein. In absence of ActD, no apoptosis-inducing activity was observed with the Cetuximab-TNFα fusion protein at concentrations below 30 ng/ml.

Example 14: In Vivo Anti-Tumor Activity of Her-2 Antibody-TNFα Fusion Protein on Her-2-Positive Mouse Melanoma B16 in Mice The C57BL/6 mice were obtained from Shanghai SLAC Laboratory Animal Co., Ltd. The animals were maintained in SPF environment.

Twenty 6-7 weeks old male C57/B6 mice were divided into 4 groups of 5 animals/group. The animals were subcutaneously injected with B16/Her-2 cells ($1\times10^6$ cells/animal) at axilla. When the tumor reached 200-600 mm$^3$, the mice were injected intravenously with the Trastuzumab-TNFα fusion protein or Trastuzumab at different dosages. There were two dosage groups for the Trastuzumab-TNFα fusion protein: 1 mg/kg and 3 mg/kg; one group for Trastuzumab: 3 mg/kg; and one group of control: injection of even volumes of PBS. The treatments were administrated twice a week for two weeks, i.e., totally of 4 dosings. Tumor volume was measured and animals weighed at each dosing. 4 days after the last dosing, the mice were sacrificed by cervical dislocation. Orbital vein blood was collected, tumor weight and spleen weight and size were recorded, and tumors were pictured via anatomy.

Results and Analysis

Figure 13:
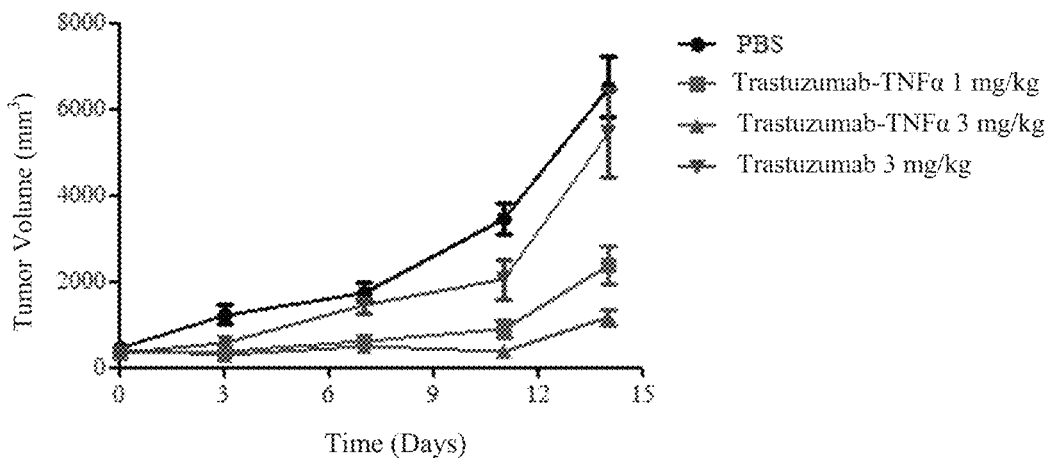
FIG. 13: Her-2 antibody-TNFα fusion protein inhibited growth of mouse melanoma B16 expressing human Her-2 in mouse. C57/B6 mice were grafted with the mouse melanoma B16 expressing human Her-2 on back. The mice were treated via caudal intravenous injection. Tumor volume was measured and calculated as (length×width×width/2).

As shown in FIG. 13, the Trastuzumab-TNFα fusion protein effectively inhibited growth of B16/Her-2 tumor in mice, with an inhibition rate of 63% for the dosage of 1 mg/kg and 82% for the dosage of 3 mg/kg in a proportional relation to the dosages. Trastuzumab at 3 mg/kg exhibited a fairly low effect on tumor growth, with an inhibition rate of 16%, which is far lower than the efficacy of the fusion protein at corresponding dosage.

Meanwhile, change in bodyweight was taken as a measurement of toxicity of the fusion protein in mouse. Weight of the animals dropped by about 10% three days after the first administration, then stayed and began to recover during the continuous administration. This suggests that the toxicity of the fusion protein at 3 mg/kg is temporary and reversible.

Example 15: In Vivo Anti-Tumor Activity of Her-2 Antibody-TNFα Fusion Protein on Her-2-Positive Mouse Colon Carcinoma CT26 in Mice The Balb/c mice were obtained from Shanghai SLAC Laboratory Animal Co., Ltd. Twenty one 6-7 weeks old male Balb/c mice were divided into 5 groups of 4 or 5 animals/group. The animals were subcutaneously grafted with CT26/Her-2 cells ($1\times10^6$ cells/animal) on back. When the tumor reached 100-400 mm$^3$, the mice were injected intravenously with the antibody-TNFα fusion protein at different dosages: 0.1 mg/kg, 0.3 mg/kg, 1 mg/kg and 3 mg/kg. The control group was injected with even volumes of PBS. The treatments were administrated three or four times a week for two weeks. Tumor volume was measured and animals weighed at each dosing. 6 days after the fourth dosing, the mice were sacrificed by cervical dislocation, and bodyweight, tumor volume and weight were recorded.

The in vivo anti-tumor effect of the Trastuzumab-TNFα fusion protein on the CT26/Her-2 tumor was further compared with that of the Trastuzumab+TNFα mixture. Twenty four 6-7 weeks old male Balb/c mice were divided into 3 groups of 8 animals/group. The animals were subcutaneously grafted with CT26/Her-2 cells ($1\times10^6$ cells/animal) on back. When the tumor reached 100-400 mm$^3$, the three groups were injected intravenously with 0.2 ml PBS, Trastuzumab-TNFα fusion protein (3 mg/kg) and the Trastuzumab+TNFα mixture (3 mg/kg, the weight ratio of Trastuzumab to TNFα (dimeric) being 4:1). In the Trastuzumab+TNFα mixture, the molar ratio of Trastuzumab to TNFα was 1:2, the same as in the Trastuzumab-TNFα fusion protein. Two doses were given, with an interval of three weeks. Tumor volume and body-weight were recorded at each dosing.

Results and Analysis

Figure 14A:
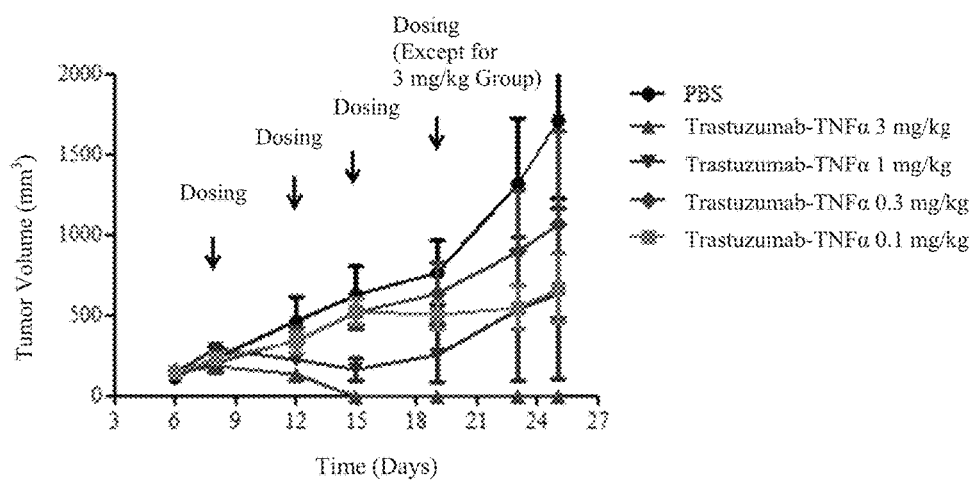
FIGS. 14A-14B: Her-2 antibody-TNFα fusion protein inhibited growth of mouse colon cancer cells CT26 expressing human Her-2 in mice.

As shown in FIG. 14A, in the mice treated with the fusion protein, hemolysis was observed in tumors. As few as 2 doses of 3 mg/kg Trastuzumab-TNFα fusion protein were need to produce hemolysis and necrosis in all tumors, and finally elimination of tumors. After four continuous dosings, in the group treated with the 1 mg/kg dosage, two animals were observed with elimination of tumors, one with a tumor volume ⅕ of that in the PBS group and the other with a tumor volume comparable with the PBS group. In the group treated with the 0.3 mg/kg dosage, two animals were observed with almost elimination of tumors, with the average of tumor volume being 1/10 to 1/20 of that in the PBS group, and the other two with a tumor volume comparable with the PBS group. In the group treated with the 0.1 mg/kg dosage, two animals were observed with tumor reduction, with an average of tumor volume being around ⅕ of that in the PBS group, and the other two with an average of tumor volume being around ½ of that in the PBS group.

As shown by these results, the Her-2 antibody-TNFα fusion protein can effectively inhibit growth of the CT26/Her-2 tumor and render a complete elimination of tumors in mice, producing an anti-tumor activity even at a dosage as low as 0.1 mg/kg.

Figure 14B:
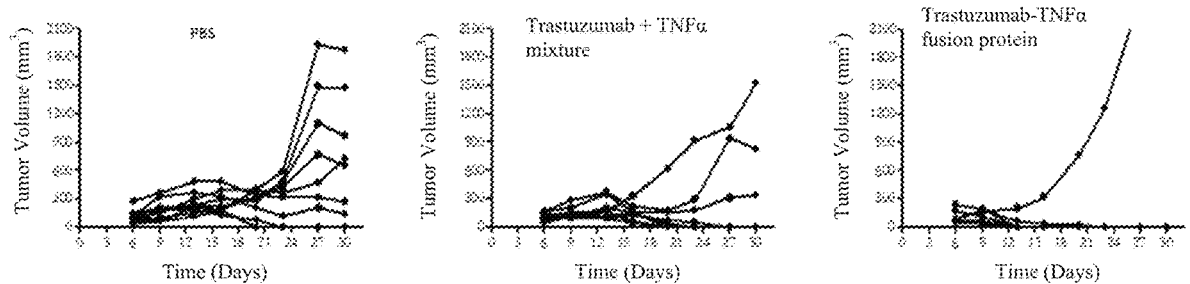

The Trastuzumab-TNFα fusion protein was found far more efficacious than the Trastuzumab+TNFα mixture in inhibiting growth of the CT26/Her-2 tumor. The next day of second dosing (D13), in the group treated with 3 mg/kg of Trastuzumab-TNFα fusion protein, the average tumor volume was 33 mm$^3$, while in the group of the Trastuzumab+TNFα mixture at a corresponding dosage, the average was 195 mm$^3$, with inhibition rates being respectively 87% and 24% (relative to the average tumor volume in the PBS group being 257 mm$^3$). The result was statistically significant, $p<0.004$ in both cases (FIG. 14B). At D30, in the group of Trastuzumab-TNFα fusion protein, complete elimination of tumor were was observed in all animals except for one; while in the group of Trastuzumab+TNFα mixture, tumors growth remained detectable in three animals.

Description of Sequences

| SEQ ID NO: | Name |
| --- | --- |
| 1 | Sequence encoding Trastuzumab's heavy chain-TNFα |
| 2 | Amino acid sequence of Trastuzumab's heavy chain-TNFα |
| 3 | Sequence encoding Trastuzumab's light chain |
| 4 | Amino acid sequence of Trastuzumab's light chain |
| 5 | Primer M13-F |
| 6 | Primer KDP004 |
| 7 | Primer KDP045 |
| 8 | Primer TNF-R |
| 9 | Primer M13-R |
| 10 | Primer KDP077 |
| 11 | Primer KDP020 |
| 12 | Primer BGH-R |
| 13 | Primer KDP092 |

| SEQ ID NO: | Name |
|---|---|
| 14 | Primer KDP093 |
| 15 | Primer CMV-P |
| 16 | Primer KDP033 |
| 17 | Primer KDP094 |
| 18 | Primer KDP010 |
| 19 | Sequence encoding Cetuximab's heavy chain-TNFα |
| 20 | Amino acid sequence of Cetuximab's heavy chain-TNFα |
| 21 | Sequence encoding Cetuximab's light chain |
| 22 | Amino acid sequence of Cetuximab's light chain |

The invention claimed is:

1. A fusion protein of an antibody and TNFα, comprising an antibody moiety and a TNFα moiety conjugated to the C-terminal of the heavy chain of said antibody, wherein said fusion protein comprises: a heavy chain comprising the heavy chain of said antibody with said TNFα moiety linked at the C-terminal and optionally a signal peptide at N-terminal; and a light chain comprising the light chain of said antibody and optionally a signal peptide at N-terminal;

wherein the antibody moiety in the fusion protein is in the form of a full-length antibody;

wherein said antibody is specific to a tumor antigen, Her-2, the antibody is Trastuzumab, and said TNFα moiety is human TNFα.

2. The fusion protein according to claim 1, wherein the molar ratio of said antibody moiety to said TNFα moiety is 1:2.

3. The fusion protein according to claim 1, wherein the TNFα molecule has the sequence of positions 469-625 in SEQ ID NO: 2, the heavy chain of said fusion protein has the amino acid sequence of positions 20-625 or the amino acid sequence of positions 1-625 in SEQ ID NO: 2, and the light chain of said fusion protein has the amino acid sequence of positions 21-234 or the amino acid sequence of positions 1-234 in SEQ ID NO: 4.

4. A composition comprising
(i) the fusion protein according to claim 1 and, optionally,
(ii) one or more additional active agents for treating or for preventing tumors;
wherein, said one or more additional active agents for treating or preventing tumors are chemotherapeutic agents.

* * * * *